United States Patent
Kovacs et al.

(10) Patent No.: US 11,512,288 B2
(45) Date of Patent: *Nov. 29, 2022

(54) METHODS AND KITS FOR CELL ACTIVATION

(71) Applicant: General Electric Company, Schenectady, NY (US)

(72) Inventors: Ernest William Kovacs, San Diego, CA (US); Anup Sood, Niskayuna, NY (US); Reginald Donovan Smith, Niskayuna, NY (US); Evelina Roxana Loghin, Niskayuna, NY (US); Padmaparna Chaudhuri, Bangalore Karnataka (IN); Vandana Keskar, Niskayuna, NY (US); Chrystal Mae Chadwick, Niskayuna, NY (US); Martin James Brown, Niskayuna, NY (US)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 835 days.

This patent is subject to a terminal disclaimer.

(21) Appl. No.: 16/339,077

(22) PCT Filed: Aug. 24, 2017

(86) PCT No.: PCT/US2017/048306
§ 371 (c)(1),
(2) Date: Apr. 3, 2019

(87) PCT Pub. No.: WO2018/039400
PCT Pub. Date: Mar. 1, 2018

(65) Prior Publication Data
US 2020/0181572 A1   Jun. 11, 2020

Related U.S. Application Data

(63) Continuation of application No. 15/245,584, filed on Aug. 24, 2016, now Pat. No. 10,294,454.

(51) Int. Cl.
*C12N 5/0783* (2010.01)
*C07K 16/28* (2006.01)

(52) U.S. Cl.
CPC ........ *C12N 5/0636* (2013.01); *C07K 16/2809* (2013.01); *C07K 16/2818* (2013.01); *C12N 2501/51* (2013.01); *C12N 2501/515* (2013.01)

(58) Field of Classification Search
CPC .............. C12N 5/0636; C12N 2501/51; C12N 2501/515; C07K 16/2809; C07K 16/2818
See application file for complete search history.

(56) References Cited

U.S. PATENT DOCUMENTS

| | | |
|---|---|---|
| 5,506,121 A | 4/1996 | Skerra et al. |
| 5,635,602 A | 6/1997 | Cantor |
| 5,658,741 A | 8/1997 | Bolton et al. |
| 5,858,358 A | 1/1999 | June et al. |
| 5,872,222 A | 2/1999 | Chang |
| 6,077,833 A | 6/2000 | Bennett et al. |
| 6,103,493 A | 8/2000 | Skerra et al. |
| 6,106,835 A | 8/2000 | Chang |
| 6,117,982 A | 9/2000 | Chang |
| 6,129,916 A | 10/2000 | Chang |
| 6,197,298 B1 | 3/2001 | Chang |
| 6,248,564 B1 | 6/2001 | Walter et al. |
| 6,268,411 B1 | 7/2001 | Schneck et al. |
| 6,270,772 B1 | 8/2001 | Burrows et al. |
| 6,448,071 B1 | 9/2002 | Schneck et al. |
| 6,458,354 B1 | 10/2002 | Schneck et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,897,067 B2 | 5/2005 | Uhler |
| 6,902,933 B2 | 6/2005 | Uhler |
| 6,905,681 B1 | 6/2005 | June et al. |
| 7,056,741 B2 | 6/2006 | Uhler |
| 7,268,219 B1 | 9/2007 | Savage |
| 7,541,184 B2 | 6/2009 | Berenson et al. |
| 7,572,631 B2 | 8/2009 | Berenson et al. |

(Continued)

FOREIGN PATENT DOCUMENTS

| | | |
|---|---|---|
| EP | 0421380 B1 | 12/1995 |
| EP | 0 678 034 B1 | 5/1999 |

(Continued)

OTHER PUBLICATIONS

PCT International Search Report and Written Opinion for PCT Application No. PT/US2017/048306 dated Nov. 16, 2017 (11 pages).
Abendroth, F., et al., "DNA-controlled bivalent presentation of ligands for the estrogen receptor," Angewandte Chemie International Edition, vol. 50, pp. 8592-8596 (2011).
"Adaptimmune gains licensing rights to Life Tech antibody-coated magnetic beads," Retrieved from the Internet URL: https://www.pctcelltherapy.com/industry-news/2013/01/10/adaptimmune-gains-licensing-rights-to-life-tech-antibody-coated-magnetic-beads, on Aug. 9, 2018, pp. 1-2, (Jan. 8, 2013).

(Continued)

*Primary Examiner* — Daniel E Kolker
*Assistant Examiner* — Brian Hartnett
(74) *Attorney, Agent, or Firm* — Eversheds Sutherland (US) LLP

(57) ABSTRACT

Provided herein are methods of activating immune cells. The method includes providing a population of immune cells and contacting the population of immune cells with a first agent and a second agent. The first agent includes an immune cell activator attached to a first binder moiety, and the second agent includes at least one capture oligomer. The at least one capture oligomer is capable of associating with the first binder moiety. Also provided are kits for activating immune cells.

14 Claims, 27 Drawing Sheets

Specification includes a Sequence Listing.

(56) References Cited

U.S. PATENT DOCUMENTS

| | | |
|---|---|---|
| 7,592,431 B2 | 9/2009 | Har-Noy |
| 7,927,595 B1 | 4/2011 | June et al. |
| 7,973,137 B1 | 7/2011 | Schneck et al. |
| 8,012,750 B2 | 9/2011 | Har-Noy |
| 8,617,884 B2 | 12/2013 | Berenson et al. |
| 8,637,307 B2 | 1/2014 | June et al. |
| 9,862,908 B2 | 1/2018 | Chen et al. |
| 10,294,454 B2* | 5/2019 | Kovacs ............. C07K 16/2818 |
| 2002/0051783 A1 | 5/2002 | Savage |
| 2002/0058019 A1 | 5/2002 | Berenson et al. |
| 2002/0091079 A1 | 7/2002 | Rhode et al. |
| 2002/0115214 A1 | 8/2002 | June et al. |
| 2002/0122818 A1 | 9/2002 | Albani |
| 2002/0127231 A1 | 9/2002 | Schneck et al. |
| 2002/0198144 A1 | 12/2002 | Wong et al. |
| 2003/0044415 A1 | 3/2003 | Savage |
| 2003/0072796 A1 | 4/2003 | Cai et al. |
| 2003/0083474 A1 | 5/2003 | Schmidt |
| 2003/0119185 A1 | 6/2003 | Berenson et al. |
| 2003/0127382 A1 | 7/2003 | Miltenyi et al. |
| 2003/0224520 A1 | 12/2003 | June et al. |
| 2003/0229020 A1 | 12/2003 | Yuqiu et al. |
| 2003/0235908 A1 | 12/2003 | Berenson et al. |
| 2004/0001829 A1 | 1/2004 | June et al. |
| 2004/0005298 A1 | 1/2004 | Bonyhadi et al. |
| 2004/0028692 A1 | 2/2004 | Zitvogel |
| 2004/0082012 A1 | 4/2004 | Busch et al. |
| 2004/0091488 A1 | 5/2004 | Seeman et al. |
| 2004/0096429 A1 | 5/2004 | Savage |
| 2004/0115216 A1 | 6/2004 | Schneck et al. |
| 2004/0137617 A1 | 7/2004 | Luxembourg et al. |
| 2004/0151704 A1 | 8/2004 | Berenson et al. |
| 2004/0175373 A1 | 9/2004 | Berenson et al. |
| 2004/0203155 A1 | 10/2004 | June et al. |
| 2004/0209295 A1 | 10/2004 | Schwabe et al. |
| 2004/0224402 A1 | 11/2004 | Bonyhadi et al. |
| 2005/0084967 A1 | 4/2005 | Berenson et al. |
| 2005/0175583 A1 | 8/2005 | Tamarkin et al. |
| 2005/0191291 A1 | 9/2005 | Har-Noy |
| 2005/0214274 A1 | 9/2005 | Har-Noy |
| 2006/0013832 A1 | 1/2006 | June et al. |
| 2006/0099177 A1 | 5/2006 | June et al. |
| 2006/0140919 A1 | 6/2006 | June et al. |
| 2006/0205069 A1 | 9/2006 | June et al. |
| 2006/0246587 A1 | 11/2006 | June et al. |
| 2007/0036783 A1 | 2/2007 | Humeau et al. |
| 2007/0172490 A1 | 7/2007 | Scholz |
| 2008/0038282 A1 | 2/2008 | Napper et al. |
| 2008/0207485 A1 | 8/2008 | Schwabe |
| 2008/0279836 A1 | 11/2008 | Har-Noy |
| 2009/0017000 A1 | 1/2009 | Cai et al. |
| 2009/0155836 A1 | 6/2009 | June et al. |
| 2010/0068193 A1 | 3/2010 | Brunsvig et al. |
| 2010/0143905 A1 | 6/2010 | Lane et al. |
| 2010/0226854 A1 | 9/2010 | Schoeller et al. |
| 2010/0284965 A1 | 11/2010 | Fahmy et al. |
| 2011/0014217 A1 | 1/2011 | Fahmy et al. |
| 2011/0318380 A1 | 12/2011 | Brix et al. |
| 2012/0045767 A1 | 2/2012 | Lau et al. |
| 2013/0052733 A1 | 2/2013 | Chang |
| 2013/0171668 A1 | 7/2013 | Loeset et al. |
| 2013/0289253 A1 | 10/2013 | Luescher et al. |
| 2014/0087462 A1* | 3/2014 | Scheffold ............. C12N 5/0636 435/375 |
| 2014/0295458 A1 | 10/2014 | Schmidt et al. |
| 2014/0349315 A1 | 11/2014 | Loeset et al. |
| 2014/0370099 A1 | 12/2014 | Green et al. |
| 2015/0017721 A1* | 1/2015 | Muller ................. C12N 5/0646 435/375 |
| 2015/0024411 A1 | 1/2015 | Stadler |
| 2015/0166997 A1 | 6/2015 | Messmer |
| 2015/0366991 A1 | 12/2015 | Schneck et al. |
| 2016/0017058 A1 | 1/2016 | Kim et al. |
| 2016/0024470 A1 | 1/2016 | Aarvak et al. |
| 2016/0051698 A1 | 2/2016 | Schneck et al. |
| 2016/0068811 A1* | 3/2016 | Kokaji ................. C12N 5/0636 435/372.3 |
| 2016/0129133 A1 | 5/2016 | McCreedy |
| 2018/0057791 A1 | 3/2018 | Kovacs et al. |

FOREIGN PATENT DOCUMENTS

| | | |
|---|---|---|
| EP | 1 497 428 A2 | 1/2005 |
| EP | 0 824 594 B1 | 4/2005 |
| EP | 1 526 171 A1 | 4/2005 |
| EP | 1 330 516 B1 | 1/2007 |
| EP | 1 093 465 B1 | 9/2007 |
| EP | 1 989 292 A2 | 11/2008 |
| EP | 1 123 086 B1 | 3/2010 |
| EP | 1 594 958 B1 | 10/2010 |
| EP | 1 586 655 B1 | 7/2012 |
| EP | 1 434 856 B1 | 7/2013 |
| EP | 2 034 009 B1 | 1/2014 |
| WO | 1994012196 A1 | 6/1994 |
| WO | 1994/015635 A1 | 7/1994 |
| WO | 1994029436 A1 | 12/1994 |
| WO | 1995033823 A1 | 12/1995 |
| WO | 1998010284 A1 | 3/1998 |
| WO | 2002/042447 A2 | 5/2002 |
| WO | 2003/024989 A2 | 3/2003 |
| WO | 2003/067221 A2 | 8/2003 |
| WO | 2003/089600 A2 | 10/2003 |
| WO | 2004/065590 A2 | 8/2004 |
| WO | 20050049085 A1 | 6/2005 |
| WO | 2007/110785 A2 | 10/2007 |
| WO | 2012/024695 A1 | 2/2012 |
| WO | 20140076277 A1 | 5/2014 |
| WO | 20150158868 A3 | 1/2016 |

OTHER PUBLICATIONS

Ali M.M. et al., "Rolling circle amplification: a versatile tool for chemical biology, materials science and medicine," Chemical Society Reviews, vol. 43, No. 10, pp. 3324-3341, (May 2014).

Dako Products, "Retrieved from the Internet URL: http://www.dako.com/08065_15dec05_guide_to_flow_cytometry_mhc_multimers_chapter12.pdf, on Jul. 31, 2018, pp. 1-3 (Jul. 2018)".

Fauser, A.A., "Long-term expression of gene Introduction into normal human T-lymphocytes by retroviral-mediated gene transfer," Journal of Cellular Biochemistry, vol. 45, Issue 4, pp. 353-358, (1991) (Abstract).

Kim, C. H., et al., "Synthesis of Bispecific Antibodies using Genetically Encoded Unnatural Amino Acids," Journal of the American Chemical Society, vol. 134, pp. 9918-9921 (2012).

Ledbetter, J. A., et al., "CD28 Ligation in T-cell Activation: Evidence for Two Signal Transduction Pathways," Blood, vol. 75, No. 7, pp. 1531-1539 (Apr. 1990).

Poltorak, M., et al., "TCR activation kinetics and feedback regulation in primary human T cells," Cell Communication and Signaling, Retrieved from the Internet URL: http://www.biosignaling.com/content/pdf/1478-811X-11-4.pdf, on Jul. 31, 2017 pp. 1-11 (2013).

Sharpe, M., and Mount, N., "Genetically modified T cells in cancer therapy: opportunities and challenges," Disease Models & Mechanisms, Retrieved from the Internet URL: http://dmm.biologists.org/content/dmm/8/4/337.fµLI.pdf, on Jul. 31, 2018, pp. 337-350 (2015).

Taylor, L. P., et al., "Phenobarbital rheumatism in patients with brain tumor," Annals of Neurology, vol. 25, No. 1, pp. 92-94 (Jan. 1989).

Zhang, Z., et al., "DNA-scaffolded multivalent ligands to modulate cell function," Chembiochem, vol. 15, No. 9, pp. 1268-1273, (2014).

"Life Technologies Enters into an Exclusive License and Supply Agreement for Dynabeads," Life Technologies Corporation, Retrieved from the Internet URL:https://www.prnewswire.com/news-releases/life-technologies-enters-into-an-exclusive-license-and-supply-agreement-for-dynabeads-217738051.html, on Aug. 9, 2018, pp. 1-4, (Jul. 31, 2013).

Ceuppens et al., "Monoclonal Antibodies to the CD5 Antigen can Provide the Necessary Second Signal for Activation of Isolated Resting T cells by Solid-Phase-Bound OKT3", The Journal of Immunology, vol. 137, Issue 6, pp. 1816-1821, Sep. 15, 1986.

(56) References Cited

OTHER PUBLICATIONS

Baroja et al., "The Anti-T cell Monoclonal Antibody 9.3 (anti-CD28) Provides a Helper Signal and Bypasses the Need for Accessory Cells in T cell Activation with Immobilized Anti-CD3 and Mitogens", Cellular Immunology, vol. 120, Issue 1, pp. 205-217, Apr. 1989.

Riddell et al., "The Use of Anti-CD3 and Anti-CD28 Monoclonal Antibodies to Clone and Expand Human Antigen-Specific T cells", Journal of Immunological Methods, vol. 128, Issue 2, pp. 189-201, Apr. 17, 1990.

Norman, "Mechanisms of Action and Overview of OKT3", Therapeutic Drug Monitoring, vol. 17, Issue 6, pp. 615-620, Dec. 1995.

Rush et al., "Efficient Priming of CD4 and CD8 T Cells by DNA Vaccination Depends on Appropriate Targeting of Sufficient Levels of Immunologically Relevant Antigen to Appropriate Processing Pathways", The Journal of Immunology, vol. 169, pp. 4951-4960, 2002.

Minquet et al., "Full Activation of the T cell Receptor Requires both Clustering and Conformational Changes at CD3", Immunity, vol. 26, Issue 1, pp. 43-54, Jan. 2007.

Dollins et al., "Assembling OX40 Aptamers on a Molecular Scaffold to Create a Receptor-Activating Aptamer", Chemistry & Biology, vol. 15, Issue 7, pp. 675-682, Jul. 21, 2008.

Dave, "Hierarchical Role of CD3 Chains in Thymocyte Development", Immunol. Rev. 232, pp. 22-33, 2009.

"IBA Announces its Partnership with Beckman Coulter for the Distribution of IBA's Streptamer Product Portfolio", Bionity, http://www.bionity.com/en/news/117192/iba-announces-its-partnership-with-beckman-coulter-for-the-distribution-of-iba-s-streptamer-product-portfolio.html, May 5, 2010.

Gangar et al., "Programmable Self-Assembly of Antibody-Oligonucleotide Conjugates as Small Molecule and Protein Carriers", Journal of American Chemical Society, vol. 134, Issue 6, pp. 2895-2897, Feb. 2012.

Abbas et al., "Activation of T lymphocytes", Immunology, Chapter 9, http://www.slideshare.net/princesa_mera/immunology-chapter-9-activation-of-t-lymphocytes, Dec. 8, 2012.

Matic et al., "Fine Tuning and Efficient T Cell Activation with Stimulatory a CD3 Nanoarrays", Nano Letters, American Chemical Society, vol. 13, pp. 5090-5097, 2013.

Essand et al., "Genetically Engineered T cells for the Treatment of Cancer", Journal of Internal Medicine, vol. 273, Issue 2, pp. 166-181, Feb. 2013.

* cited by examiner

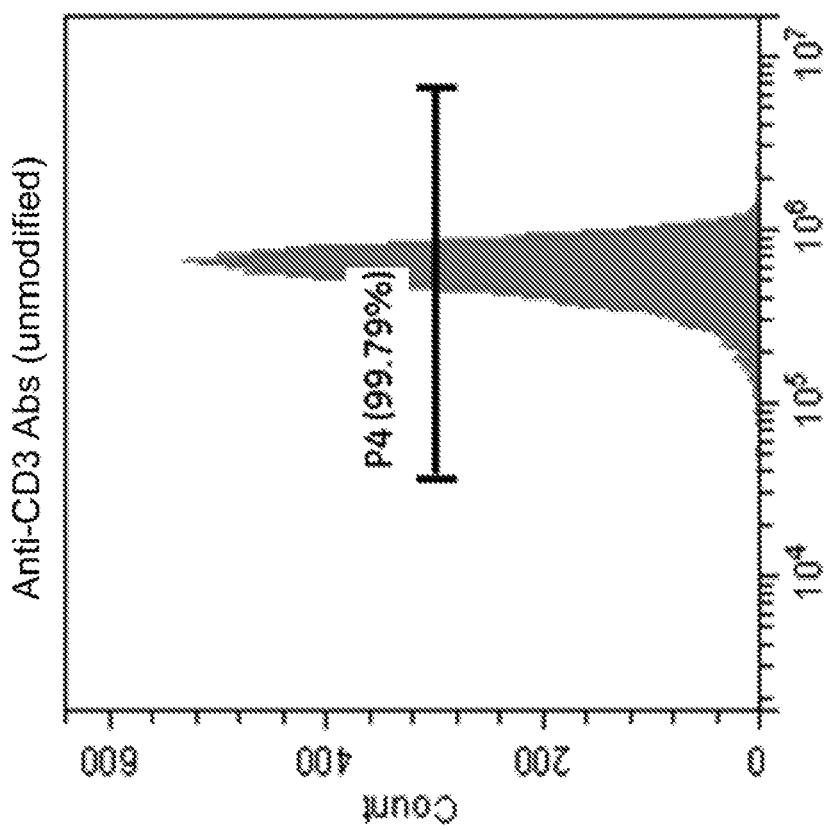
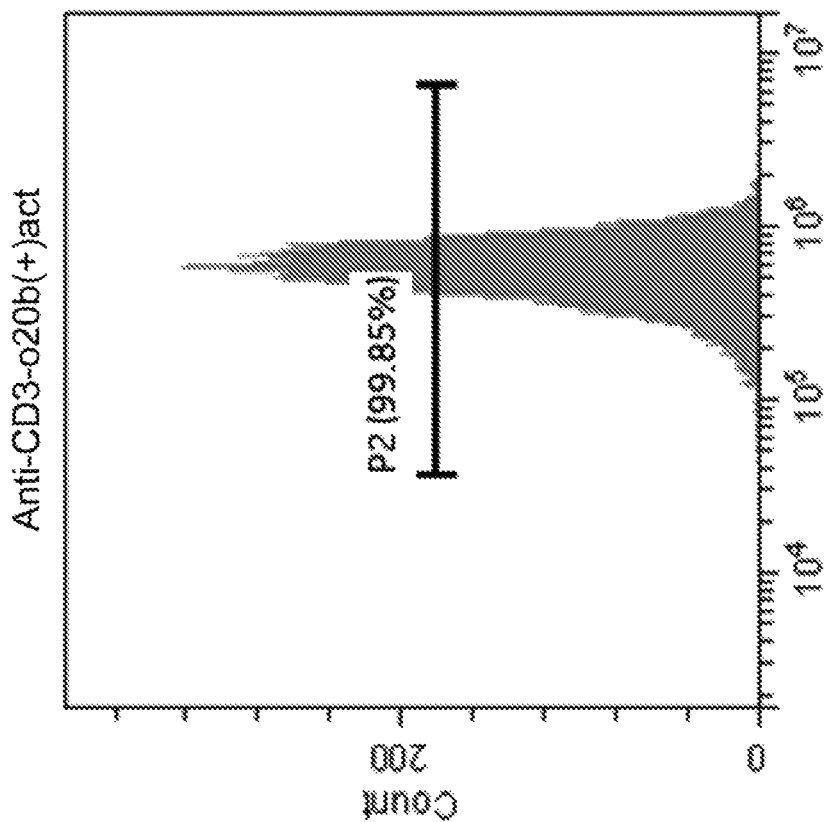

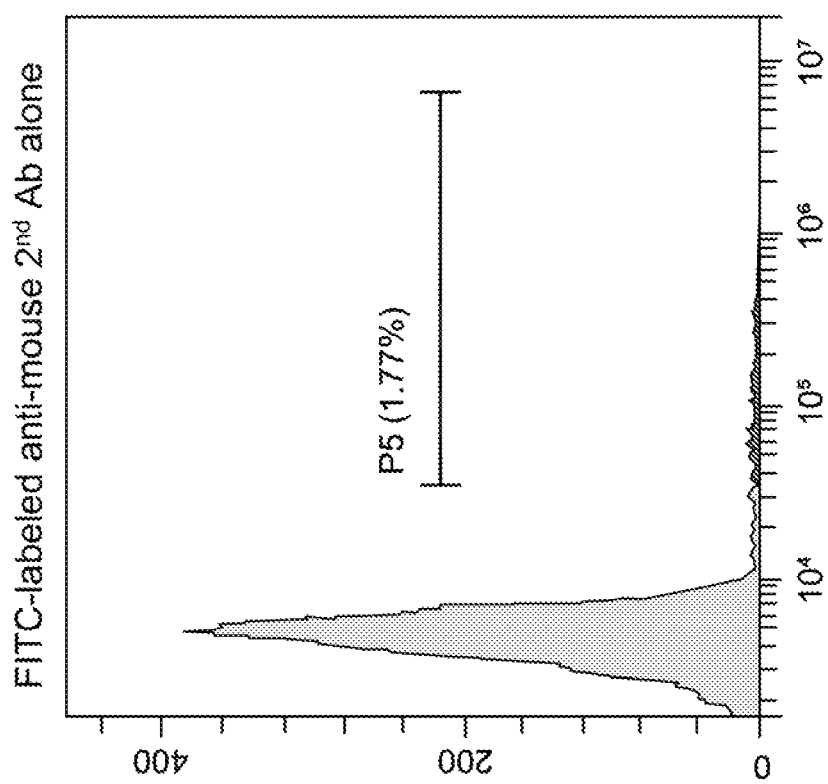

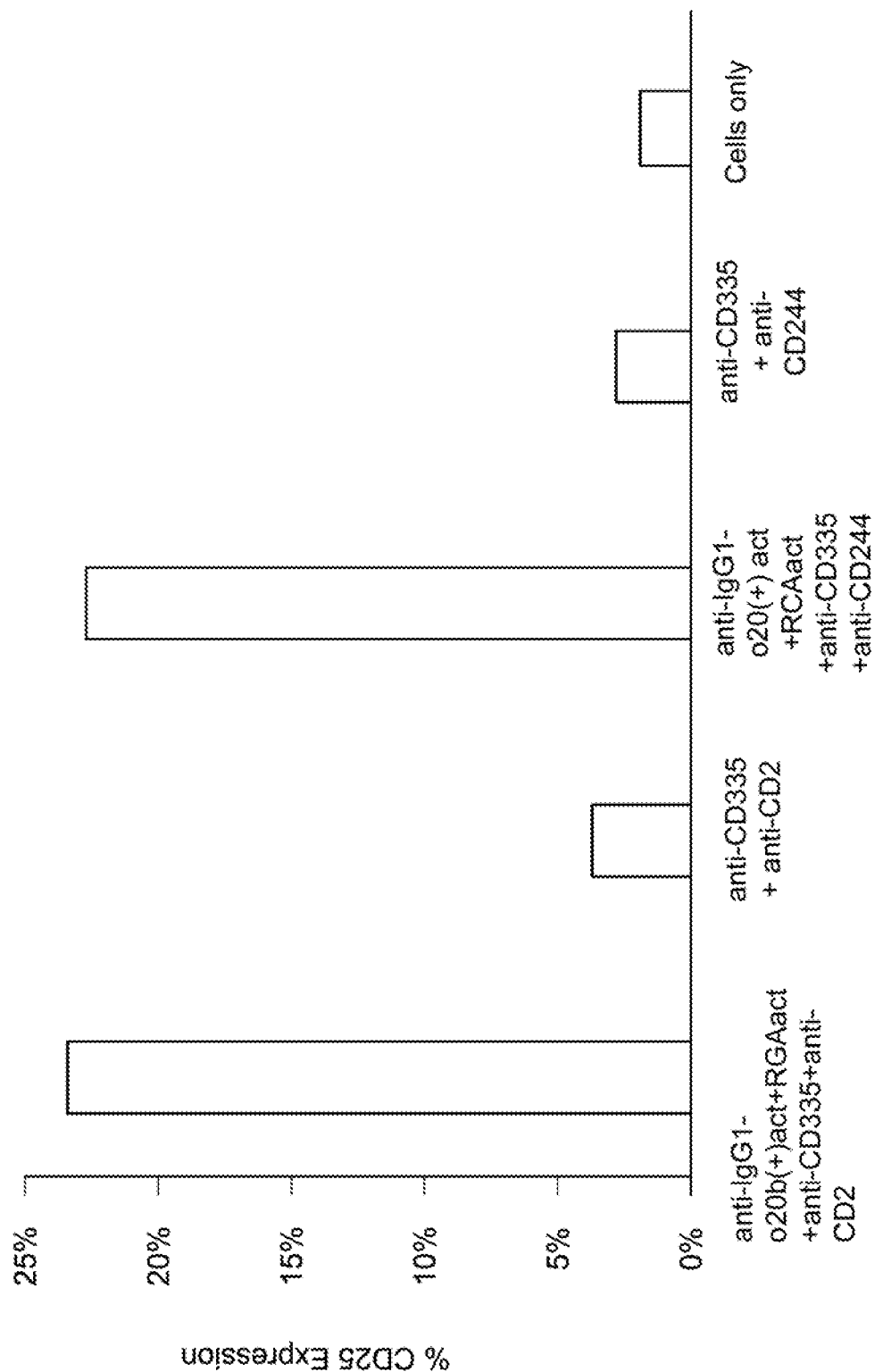

SEQUENCE LISTING

<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgactattaa gacttcctgt                                              20

<210> SEQ ID NO 2
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate

<400> SEQUENCE: 2
ttaatagtca ttccaaatat gagatgcgtt gttacaggaa gtc                    43

<210> SEQ ID NO 3
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' phosphate

<400> SEQUENCE: 3
ttaatagtca ttccaacata tgagatggtt gttacaggaa gtc                    43

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Maleimide functional group and C6 spacer

<400> SEQUENCE: 4
acaggaagtc ttaatagtca                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
atcaatgatg cataacatct                                              20

<210> SEQ ID NO 6
<211> LENGTH: 43
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: 5' phosphate

<400> SEQUENCE: 6
catcattgat ttagacactg aaaaagttcg aggagatgtt atg                    43

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Maleimide functional group and C6 spacer

<400> SEQUENCE: 7
catcattgat ttagacactg aaaaa                                        25
```

METHODS AND KITS FOR CELL ACTIVATION

CROSS REFERENCE TO RELATED APPLICATIONS

This application claims the priority benefit of PCT/US2017/048306 filed on Aug. 24, 2017 which claims priority benefit of U.S. application Ser. No. 15/245,584, filed Aug. 24, 2016, respectively. The entire contents of which are hereby incorporated by reference herein.

SEQUENCE LISTING

The instant application contains a Sequence Listing which has been submitted electronically in ASCII format and is hereby incorporated by reference in its entirety. Said ASCII copy, created on Mar. 25, 2019, is named 312704_1.txt and is 2,045 bytes in size.

FIELD OF INVENTION

The present disclosure generally relates to methods and kits for cell activation, and more specifically to methods and kits for immune cell activation.

BACKGROUND

Cellular therapies, for example T cell therapies, have shown remarkable success in treating hematological tumors and show promise in treatment of solid tumors. These therapies generally require isolation of peripheral blood mononuclear cells (PBMC) or T cells from a patient or a donor, and subsequent activation and proliferation to generate a therapeutic dose. In general, this type of personalized therapy consists of removing blood cells from cancer patients, isolating and activating immune cells, genetically modifying them to recognize and attack cancer cells, expanding the genetically modified immune cells, and introducing the expanded immune cells back into a patient's body so that the patient's immune system can take over. Activation is a critical component of the whole process as it is required for efficient introduction of genetic material for genetically modifying the immune cells and for their robust expansion.

Several technology platforms exist for the activation and expansion of immune cells, especially the T cells. For example, superparamagnetic, nonpyrogenic polystyrene beads with antibodies covalently bound to the surface e.g., Dynabeads® CD3/CD28 (Life Technologies, Beverly, Mass.), is one of the most widely used platforms for isolation, activation, and expansion of T cells. However, such bead-based platforms suffer from significant cell loss when used for cell clustering and cell activation, primarily due to the need for bead removal after cell expansion is complete. Alternate technologies that circumvent the issue of bead removal, are often not effective for cell activation, particularly in the early activation phase when viral transduction for genetic modification is generally carried out.

Cell therapy may also be performed with other immune cells such as natural killer (NK) cells, obtained from a patient or a third-party donor, or immortalized cell lines. In some aspects, NK cell-based cell therapy involves isolating NK cells from the blood of a patient or a donor, activating and expanding the natural killer cells, and administering them into the patient. Most of the existing protocols for the activation and expansion of NK cells involve co-cultivation with feeder-cells. Such feeder-cell systems are difficult to standardize and may introduce unpredictability and contamination into the cell culture.

As such, a new technology platform is desired that will provide novel approaches to cluster immune cell receptors for immune cell activation (e.g., for clustering cell surface receptors for T cell activation) and provide co-stimulatory signals to increase proliferation. Further, there is a need for feeder-cell free, synthetic activation systems, which can be designed to achieve controlled and reproducible activation of immune cells such as T cells and NK cells.

BRIEF DESCRIPTION

Some embodiments are directed towards a method of activating immune cells. The method includes providing a population of immune cells and contacting the population of immune cells with a first agent and a second agent. The first agent includes an immune cell activator attached to a first binder moiety, and the second agent includes at least one capture oligomer. The at least one capture oligomer is capable of associating with the first binder moiety.

Some embodiments are directed to a method of T cell activation. The method includes the steps of adding to a population of T cells, an anti-CD3 antibody, a first binder moiety attached to secondary antibody, and a second agent comprising at least one capture oligomer. The secondary antibody is capable of attaching with the anti-CD3 antibody, and the at least one capture oligomer is capable of associating with the first binder moiety. The population of the T cells are then incubated to activate the T cells.

Some embodiments are directed to a kit for immune cell activation. The kit includes an immune cell activator attached to a first binder nucleic acid sequence, and a capture nucleic acid polymer comprising at least one capture oligonucleotide. The at least one capture oligonucleotide is capable of associating with the first binder nucleic acid sequence.

DRAWINGS

These and other features, aspects and advantages of the present invention will become better understood when the following detailed description is read with reference to the accompanying figures.

FIG. 1A-1E are representative flow cytometry histograms for positively validated anti-CD3-o20b(+)act and anti-CD28-o20b(+)act conjugates binding to T cells. 1A: Binding of a DNA (o20b(+)act) attached anti-CD28 antibody (anti-CD28-o20b(+)act) to T cells; 1B: Binding of unattached or unmodified anti-CD28 antibody (positive control) to T cells; 1C: Binding of a DNA (o20b(+)act) attached anti-CD3 antibody (anti-CD3-o20b(+)act) to T cells; 1D: Binding of unattached or unmodified anti-CD3 antibody (positive control) to T cells; and 1E: Cells incubated with FITC-labeled secondary antibody (negative control).

FIG. 2 is an illustration of the generation of a circular DNA template from a single stranded DNA template (ssRCA) for subsequent generation of RCA products for T cell activation.

FIG. 3A is graphical representation of T cell activation using DNA-Based T cell Activation (DBTA) composition relative to the Dynabeads® Human T-Expander CD3/CD28 control (denoted as CD3/CD28 Dynabeads) at days 1 and 4, measured by CD25 expression. The DBTA composition used was DBTA[anti-CD3-o20b(+)act+unmodified anti-CD28], which includes the rolling circle amplification product, RCAact, anti-CD3 antibody attached to the first binder DNA sequence o20b(+)act (anti-CD3-o20b(+)act), and unmodified anti-CD28 antibody. Also shown are various controls including unmodified antibodies with rolling circle amplification (RCA) product, unmodified antibodies with free o20b(+)act, unmodified antibodies only, RCA product only, and cells alone ("cells only" control without activator).

FIG. 3B is a graphical representation of the same cultures as in FIG. 3A at days 4 and 7 showing cell expansion represented as number of folds of expansion (x-Fold Expansion) relative to a starting cell count.

FIG. 4A is a graphical representation showing significant activation (relative to "cells only" control) achieved with two different DBTA compositions, measured using CD25 expression. The different DBTA compositions used were i) DBTA[anti-CD3-o20b (+)act+unmodified anti-CD28], and ii) DBTA [anti-CD3-o20b(+)act+anti-CD28-o20b(+)act], which includes RCAact, anti-CD3-o20b(+)act, and anti-CD28-o20b(+)act. Also shown are the controls, Dynabeads® Human T-Expander CD3/CD28 (Life Technologies, Beverly, Mass.) (denoted as CD3/CD28 Dynabeads) and cells only control.

Figure 6A:
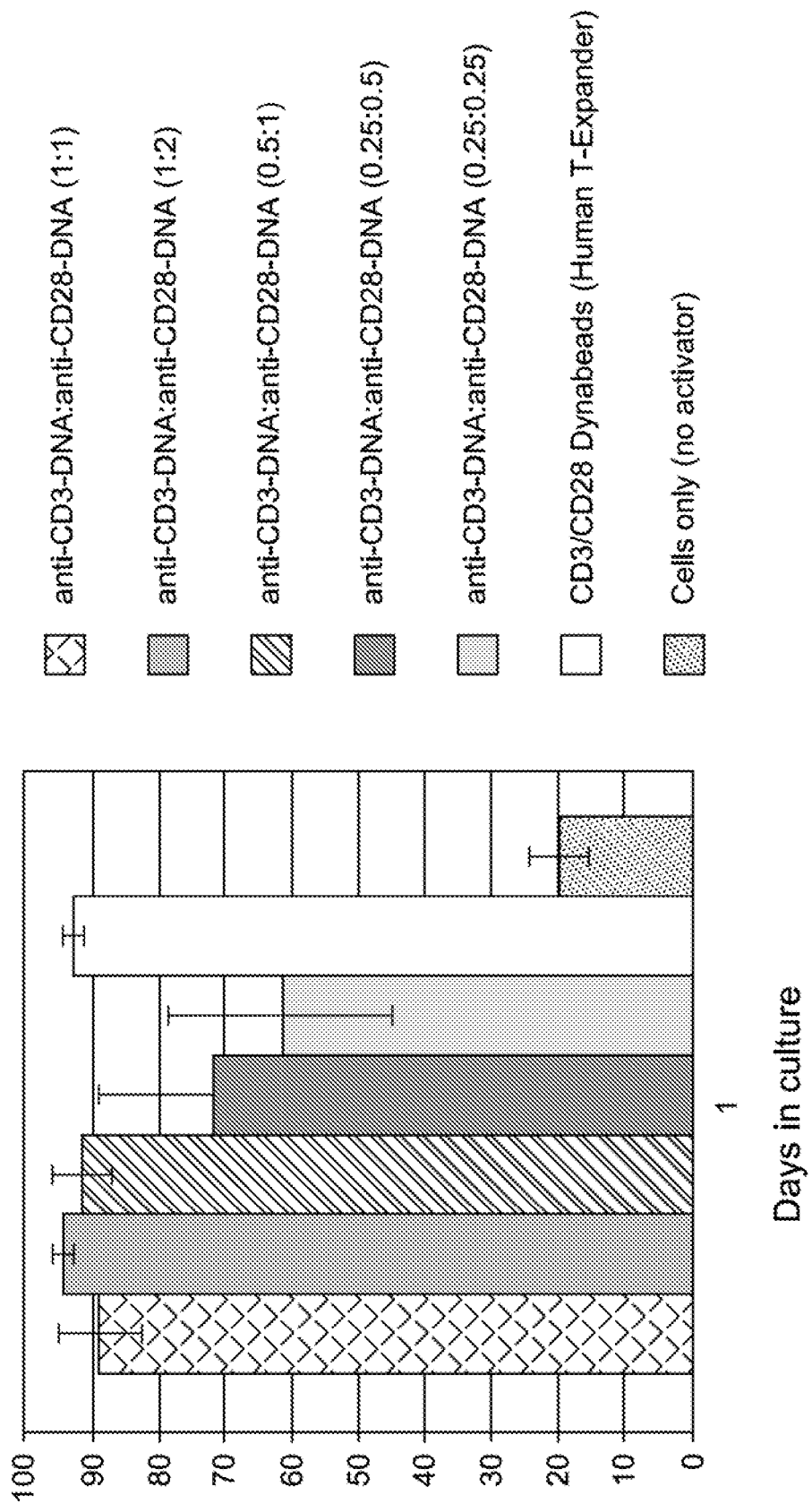

FIG. 6A is a graphical representation showing T cell activation measured by CD25 expression after 1 day in culture using DBTA[anti-CD3-o20b(+)act+anti-CD28-o20b(+)act] at different ratios of anti-CD3-o20b(+)act to anti-CD28-o20b(+)act (denoted by anti-CD3-DNA:anti-CD28-DNA in FIG) as well as different anti-CD3-o20b(+)act+anti-CD28-o20b(+)act to RCAact ratios by maintaining the same RCAact concentration (67 nM) in all cases. As shown in the figure: i) anti-CD3-DNA:anti-CD28-DNA (1:1) denotes a study where both anti-CD3-DNA and anti-CD28-DNA were at a concentration 1 µg/mL (6.7 nM), ii) anti-CD3-DNA:anti-CD28-DNA (1:2) denotes anti-CD3-DNA at concentration 1 µg/mL and anti-CD28-DNA at concentration 2 µg/mL; iii) anti-CD3-DNA:anti-CD28-DNA (0.5:1) denotes anti-CD3-DNA at concentration 0.5 µg/mL and anti-CD28-DNA at concentration 1 µg/mL; iv) anti-CD3-DNA:anti-CD28-DNA (0.25:0.5) denotes anti-CD3-DNA at concentration 0.25 µg/mL and anti-CD28-DNA at concentration 0.5 µg/mL; and v) anti-CD3-DNA:anti-CD28-DNA (0.25:0.25) denotes anti-CD3-DNA at concentration 0.25 µg/mL and anti-CD28-DNA also at concentration 0.25 µg/mL. Also shown are the controls, Dynabeads® Human T-Expander CD3/CD28 (denoted as CD3/CD28 Dynabeads) and cells only control.

Figure 6B:
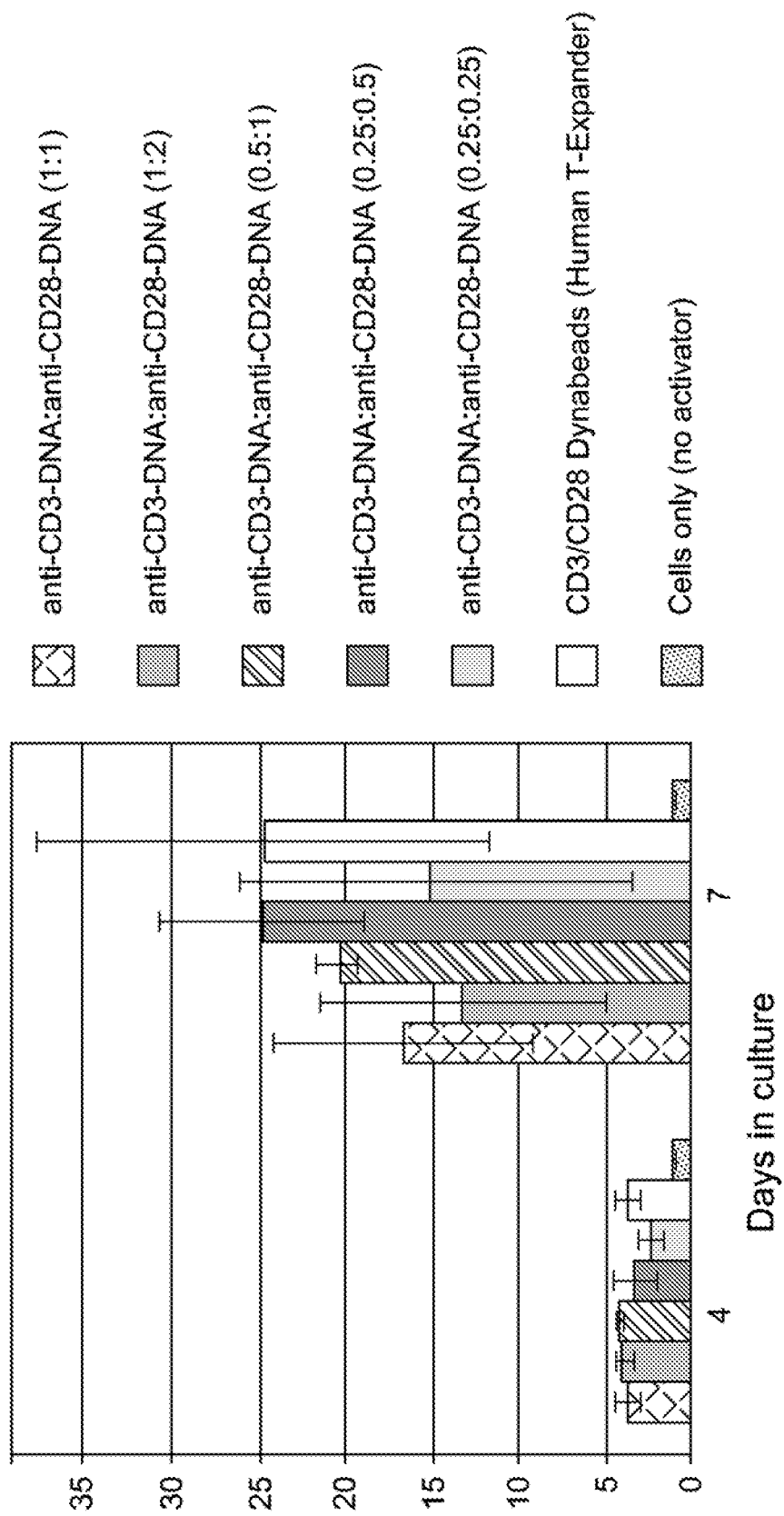

FIG. 6B is a graphical representation of cell expansion of the same cultures as in FIG. 6A after days 4 and 7 showing cell expansion represented as number of folds of expansion relative to a starting cell count.

Figure 7A:
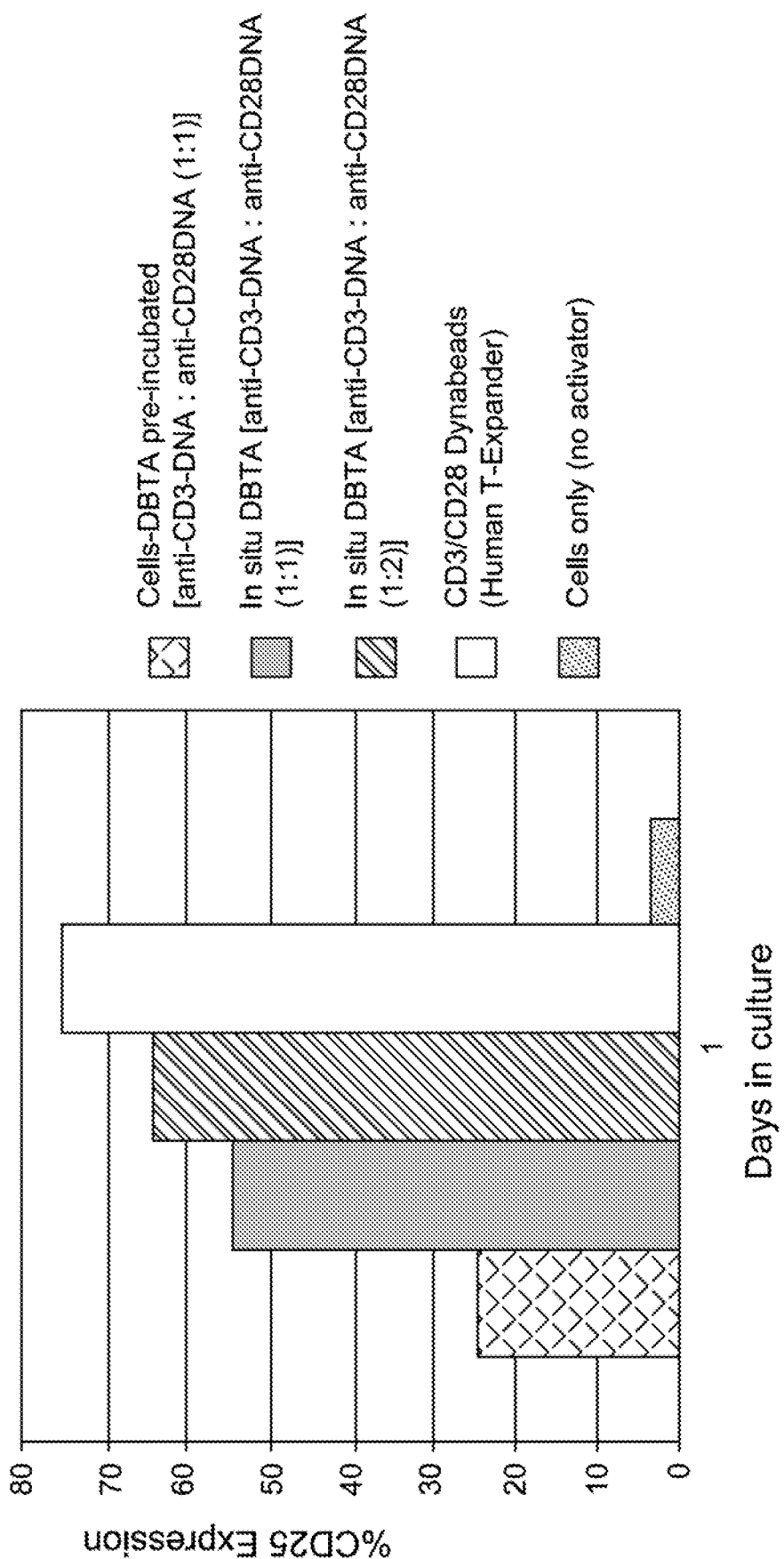

FIG. 7A is a graphical representation of T cell activation measured by CD25 expression after 24-hour in culture under three different conditions, i) cells were pre-mixed with anti-CD3-o20b(+)act and anti-CD28-o20b(+)act at anti-CD3-o20b(+)act: anti-CD28-o20b(+)act ratio 1:1, for 30 min. prior to the addition of RCAact (denoted by "cells-DBTA preincubated [anti-CD3-DNA:anti-CD28-DNA(1:1)]"), ii) all three DTBA components (RCAact, anti-CD3-o20b(+)act, and anti-CD28-o20b(+)act) were added separately to cells for in situ association at anti-CD3-o20b(+)act: anti-CD28-o20b(+)act ratio 1:1 (denoted by "in situ DBTA[anti-CD3-DNA:anti-CD28-DNA(1:1)]"), and iii) all three DTBA components (RCAact, anti-CD3-o20b(+)act, and anti-CD28-o20b(+)act) were added separately to cells for in situ association at anti-CD3-o20b(+)act: anti-CD28-o20b(+)act ratio 1:2 (denoted by "in situ DBTA[anti-CD3-DNA:anti-CD28-DNA(1:2)]"). In all cases, same RCAact concentration was maintained. The results were compared to Dynabeads® Human T-Expander CD3/CD28 (denoted as CD3/CD28 Dynabeads) and cells only as controls.

Figure 7B:
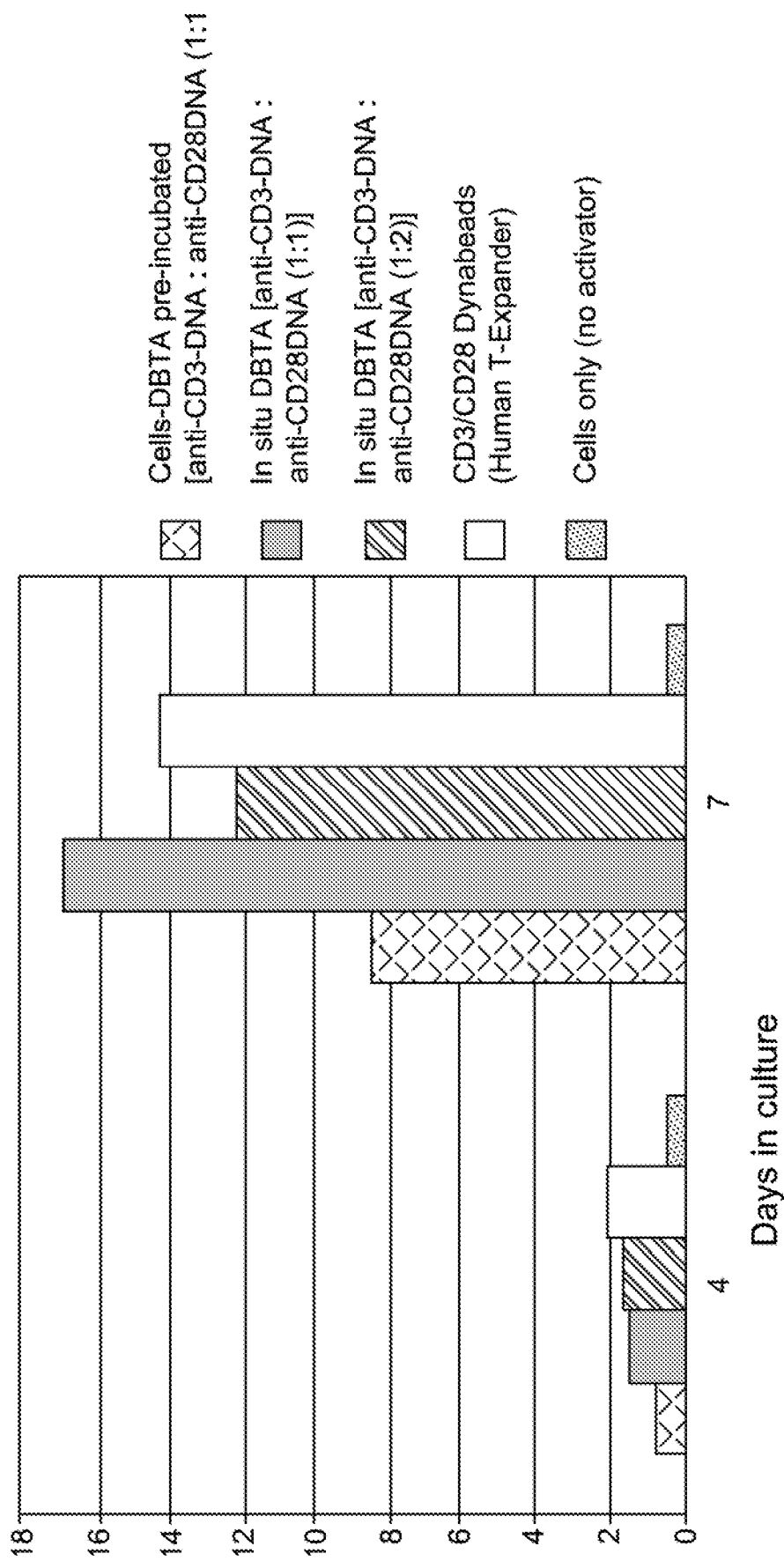

FIG. 7B is a graphical representation of the same cultures as in FIG. 7A showing the cell expansion after day 7 represented as number of folds of expansion relative to a starting cell count.

Figure 8A:
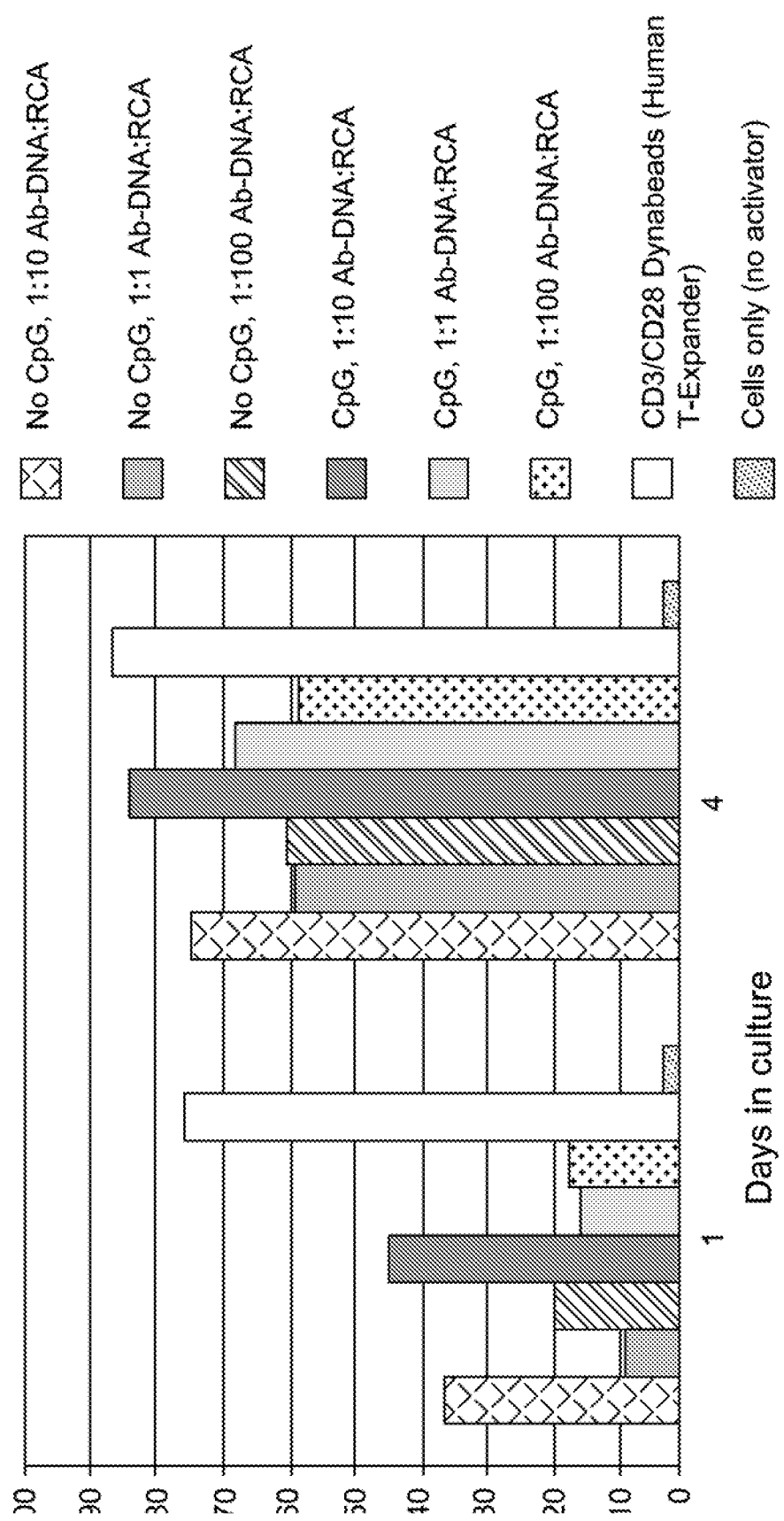

FIG. 8A is a graphical representation showing T cell activation measured by CD25 expression after days 1 and 4 of culture under culture conditions using rolling circle amplification product (RCAact) produced from RCA template containing CpG and RCAact produced from RCA template containing no-CpG. For each type of RCAact, anti-CD3-o20b(+)act: RCAact were investigated at ratios 1:1, 1:10 and 1:100. The anti-CD3-o20b(+)act: RCAact ratio has been denoted as Ab-DNA:RCA. For the rolling circle amplification product produced from RCA template containing no-CpG, the following experimental conditions were used: i) Ab-DNA: RCAact at ratio 1:10 (denoted by No CpG, 1:10 Ab-DNA: RCA); ii) Ab-DNA: RCAact at ratio 1:1 (denoted by No CpG, 1:1 Ab-DNA: RCA); and iii) Ab-DNA: RCAact at ratio 1:100 (denoted by No CpG, 1:100 Ab-DNA: RCA). Similarly, for the rolling circle amplification product produced from RCA template containing CpG, the following experimental conditions were used: i) Ab-DNA: RCAact at ratio 1:10 (denoted by CpG, 1:10 Ab-DNA: RCA); ii) Ab-DNA: RCAact at ratio 1:1 (denoted by CpG, 1:1 Ab-DNA: RCA); and iii) Ab-DNA: RCAact at ratio 1:100 (denoted by CpG, 1:100 Ab-DNA: RCA). The results were compared with Dynabeads® Human T-Expander CD3/CD28 (denoted as CD3/CD28 Dynabeads) and cells only as controls.

Figure 8B:
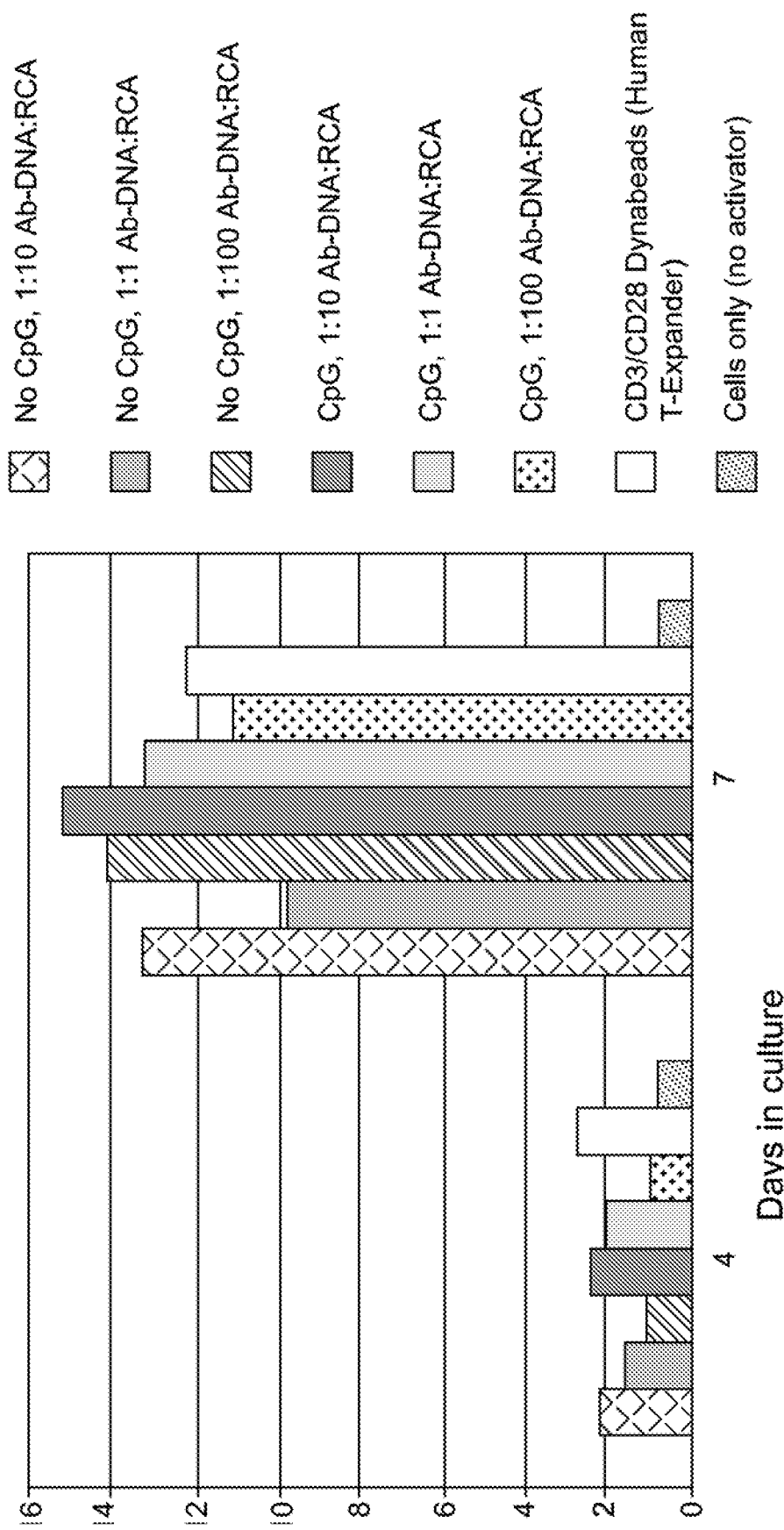

FIG. 8B is a graphical representation of the same cultures as in FIG. 8A cell expansion represented as number of folds of expansion relative to a starting cell count after 4 and 7 days.

Figure 9A:
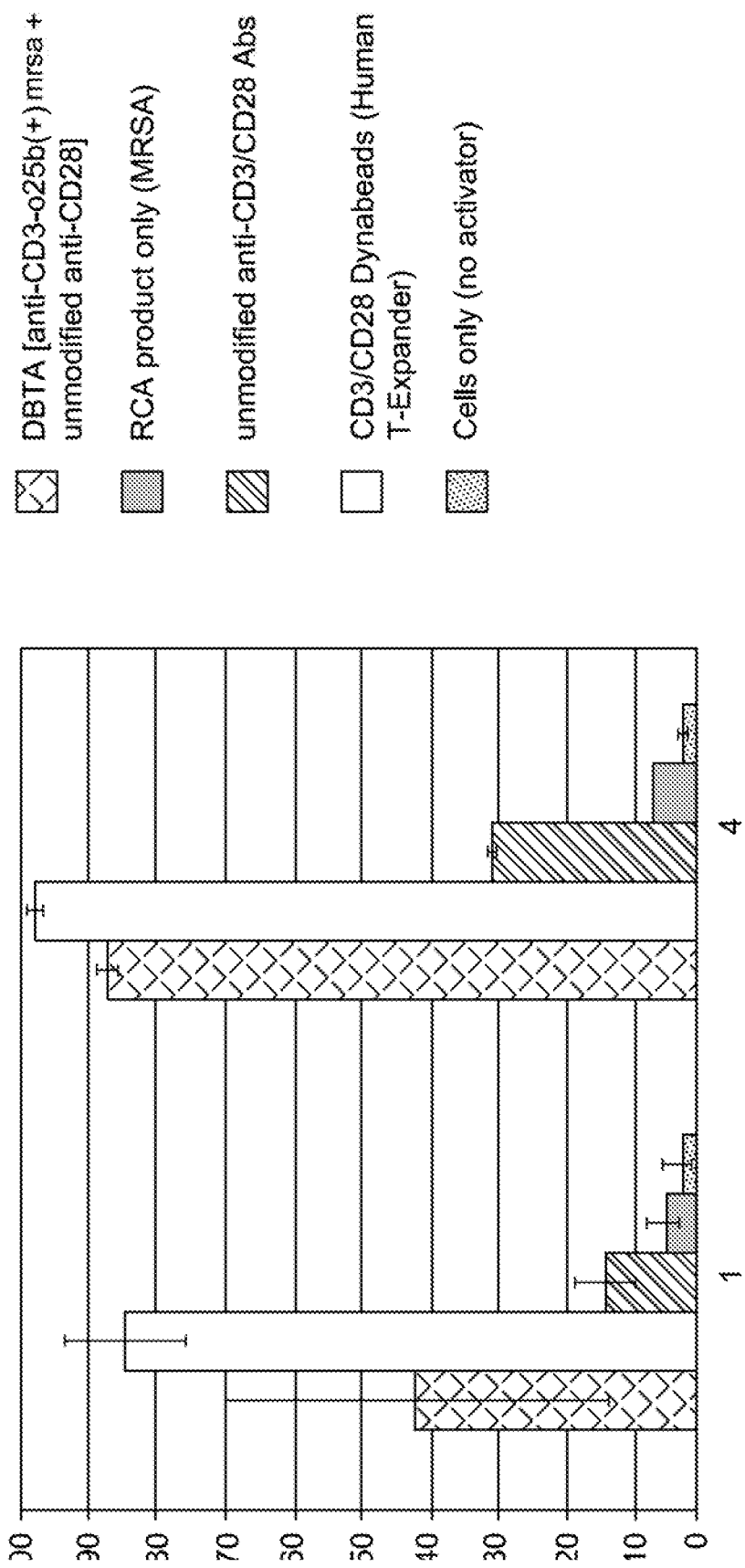

FIG. 9A is a graphical representation showing T cell activation with a portion of Methicillin-resistant *Staphylococcus aureus* (MRSA) sequence attached to the anti-CD3 antibody, its complementary RCA product, and unmodified anti-CD28 antibody, denoted by DBTA[anti-CD3-o25b(+)mrsa+unmodified anti-CD28]. The results were compared with different control conditions including RCA product only, unmodified antibodies, Dynabeads® Human T-Expander CD3/CD28 (denoted as CD3/CD28 Dynabeads) and cells only.

Figure 9B:
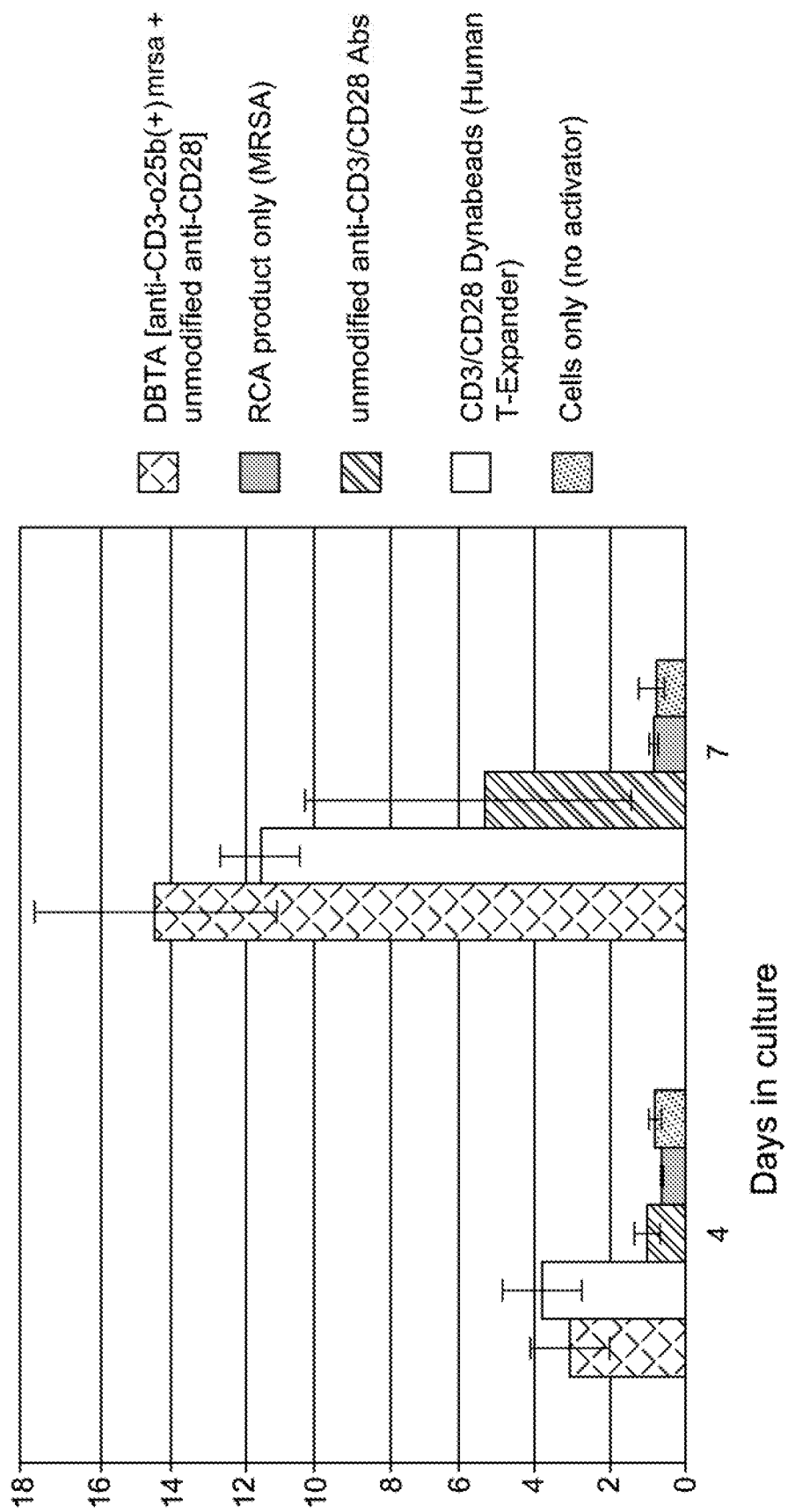

FIG. 9B is a graphical representation of the same cultures as in FIG. 9A showing cell expansion represented as number of folds of expansion relative to a starting cell count after days 4 and 7.

Figure 10A:
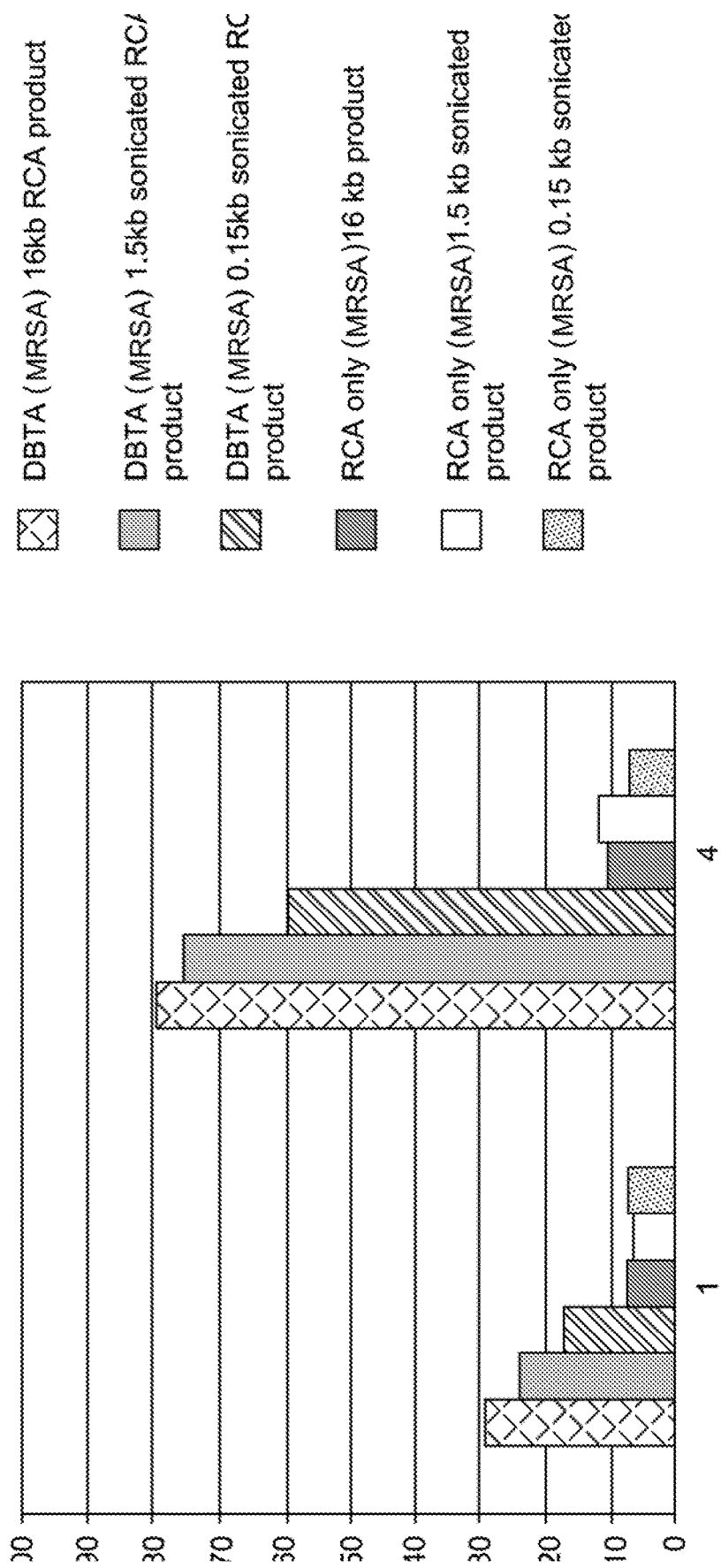

FIG. 10A is a graphical representation showing higher cell activation (% CD25 expression) when a larger rolling circle amplification (RCA) product was employed. The data is shown for RCA product derived from MRSA. i) DBTA (MRSA) 16 Kb RCA product denotes DBTA[anti-CD3-o25b(+)mrsa+unmodified anti-CD28], in which the RCA product is expected to be ~16 kilo bases (Kb); ii) DBTA (MRSA) 1.5 Kb RCA product denotes DBTA[anti-CD3-o25b(+)mrsa+unmodified anti-CD28], in which the target size of RCA product (by sonication) was 1.5 Kb; and iii) DBTA (MRSA) 0.15 Kb RCA product denotes DBTA[anti-CD3-o25b(+)mrsa+unmodified anti-CD28], in which the target size of RCA product (by sonication) was 0.15 Kb. The results were compared with controls with only the RCA products.

Figure 10B:
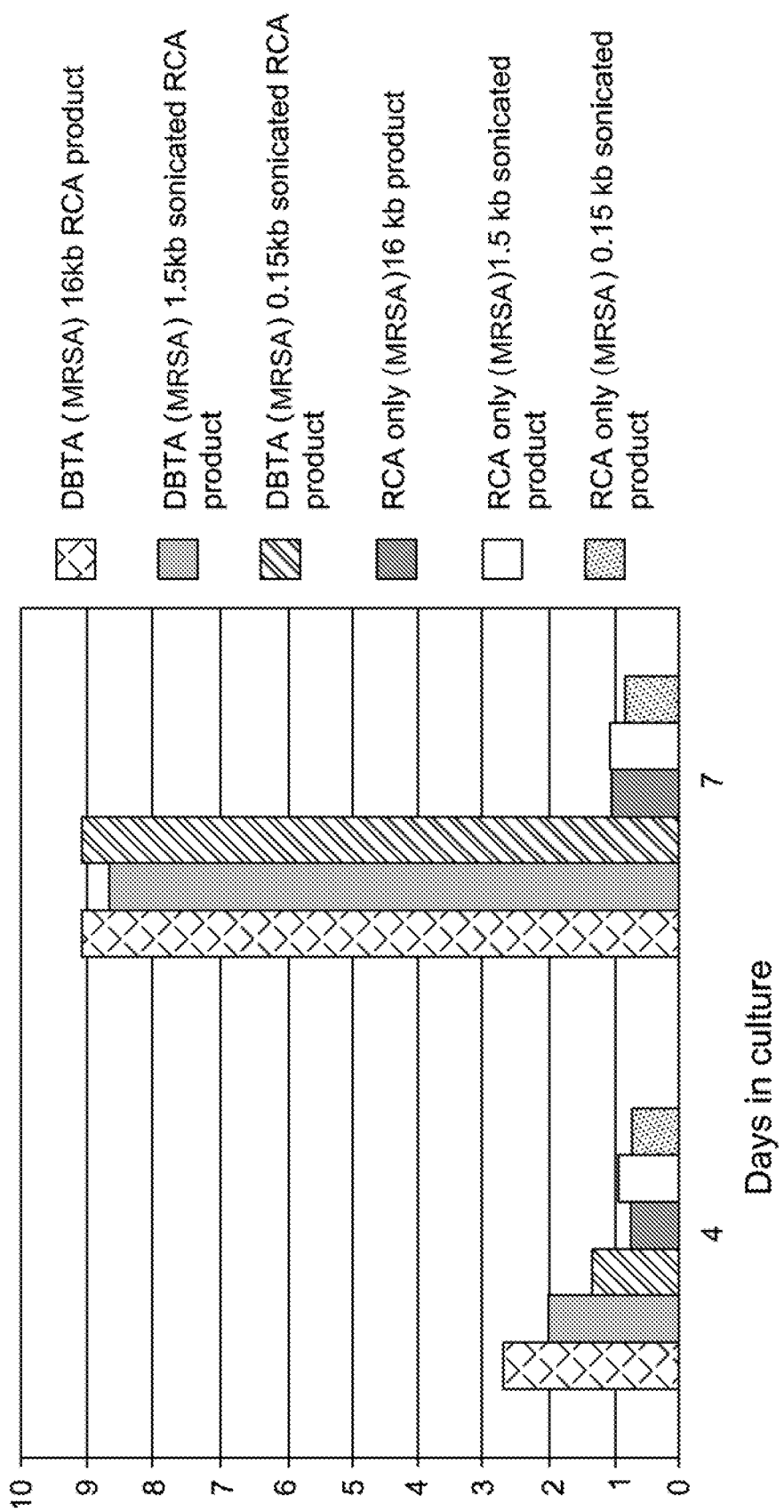

FIG. 10B is a graphical representation of the same cultures as in FIG. 10A after day 4 and day 7.

Figure 11:
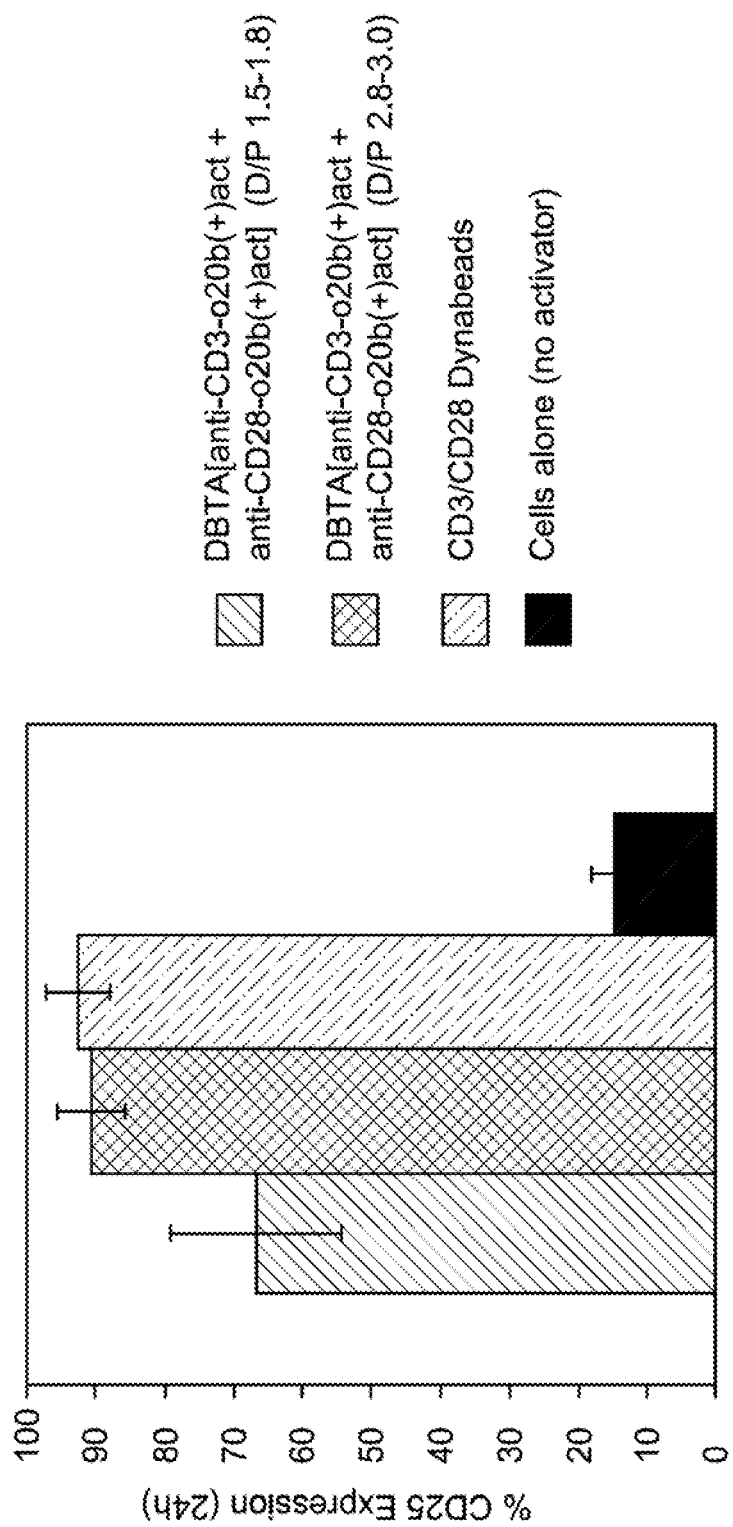

FIG. 11 shows the T cell activation measure by CD25 expression after 1 day using DBTA compositions in which the antibody-DNA conjugates were prepared by varying the DNA (D): antibody (P) ratio (D/P). i) DBTA [anti-CD3-o20b(+)act+anti-CD28-o20b(+)act] (D/P 2.8-3.0)) denotes a DBTA composition in which anti-CD3: o20b(+)act ratio is between 2.8-3.0 and anti-CD28: o20b(+) act ratio is between 2.8-3.0; and ii) DBTA [anti-CD3-o20b(+)act+anti-CD28-o20b(+)act] (D/P 1.5-1.8)) denotes a DBTA composition in which anti-CD3: o20b(+)act ratio is between 1.5-1.8 and anti-CD28: o20b(+) act ratio is between 1.5-1.8. The T cell activation was higher at higher D/P ratio. The results were compared with Dynabeads® Human T-Expander CD3/CD28 (denoted as CD3/CD28 Dynabeads) and cells only as controls. The data for FIG. 11 represents averages taken from 8 separate experiments.

Figure 12A:
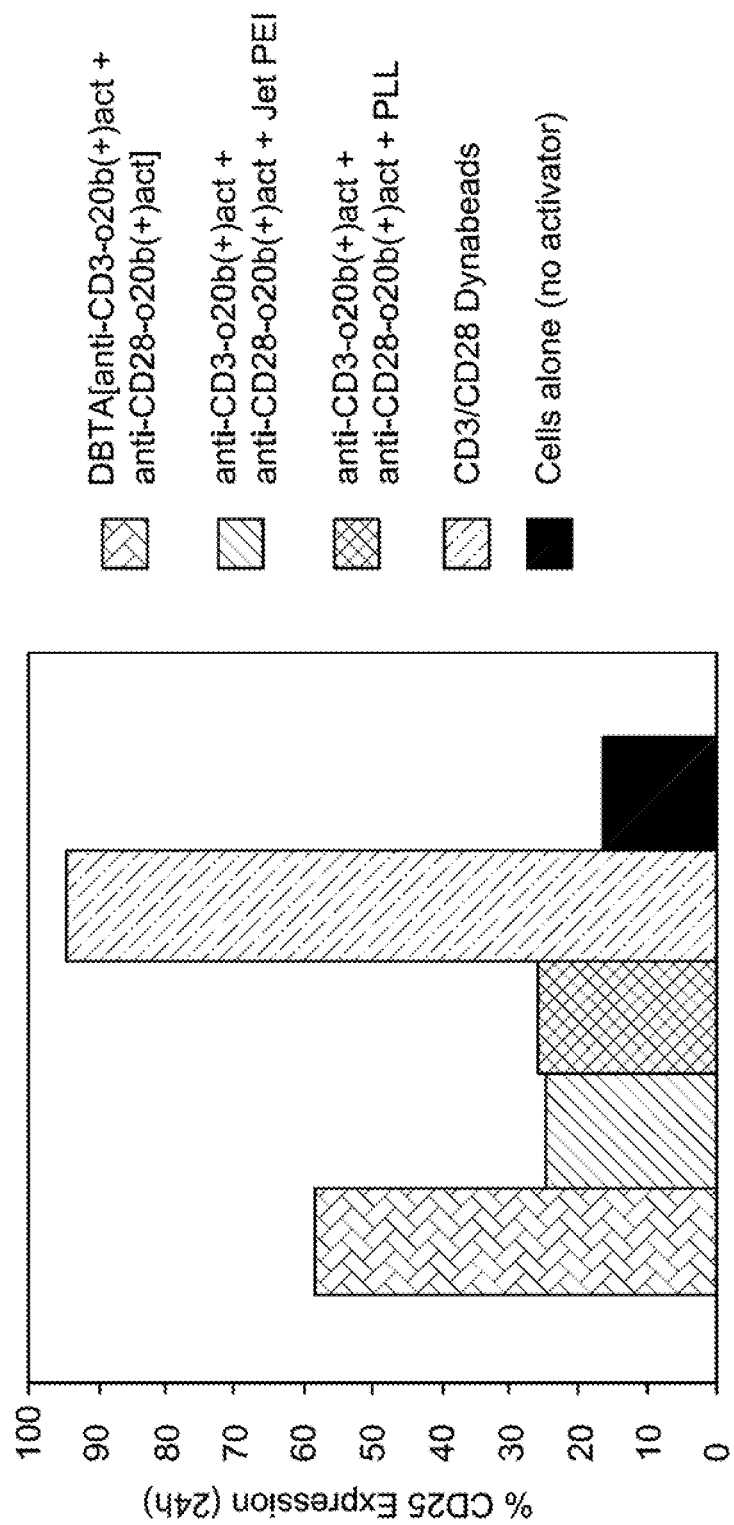

FIG. 12A shows the activation of T cells after 1 day using anti-CD3-o20b(+)act, anti-CD28-o20b(+)act, with cationic capture polymers (Jet PEI or PLL) as second agent. A DBTA composition was used as control. The experiments were conducted under the following conditions i) DBTA[anti-CD3-o20b(+)act+anti-CD28-o20b(+)act]; ii) anti-CD3-o20b(+)act+anti-CD28-o20b(+)act+Jet PEI, where polyethylenimine (PEI) was used as the cationic capture polymer; and iii) anti-CD3-o20b(+)act+anti-CD28-o20b(+)act+PLL, where poly-L-lysine (PLL) was used as the cationic capture polymer. Dynabeads® Human T-Expander CD3/CD28 (denoted as CD3/CD28 Dynabeads) and cells only samples were also used as controls.

Figure 12B:
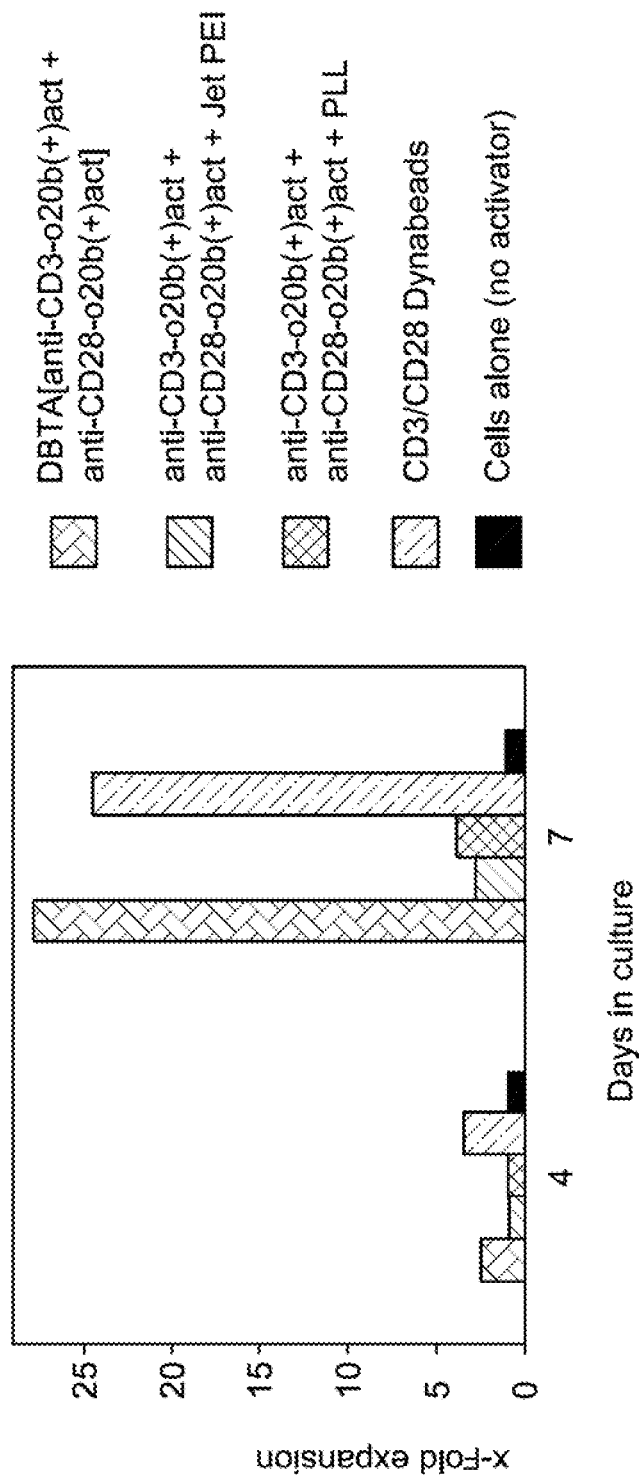

FIG. 12B is a graphical representation of the same cultures as in FIG. 12A cell expansion represented as number of folds of expansion relative to a starting cell count after 4 and 7 days.

Figure 13A:
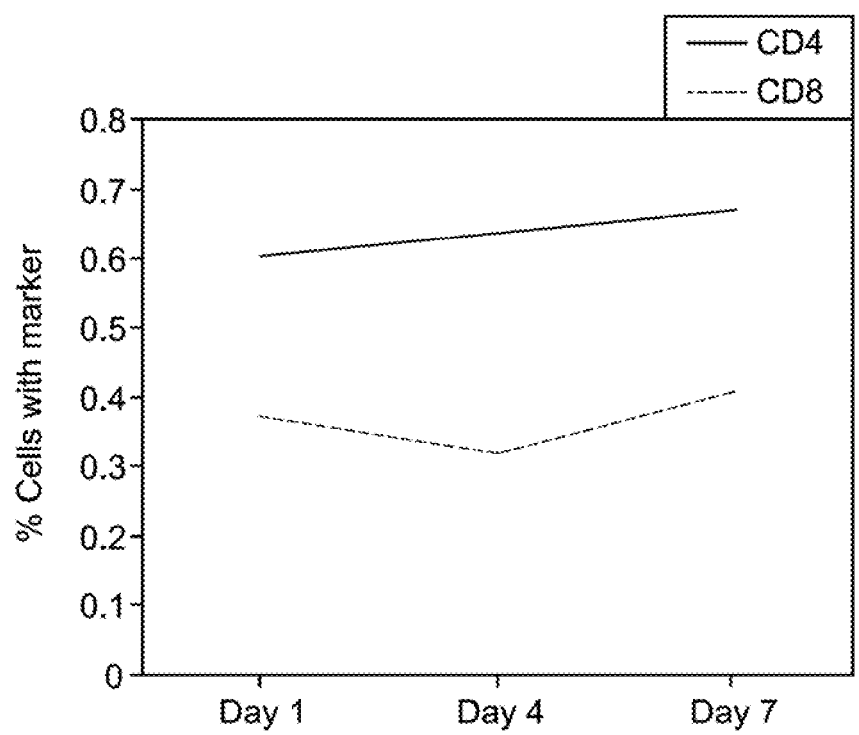

FIG. 13A shows the expansion of CD4 and CD8 T cells over a 7-day expansion period using DBTA [anti-CD3-o20b(+)act+anti-CD28-o20b(+)act].

Figure 13B:
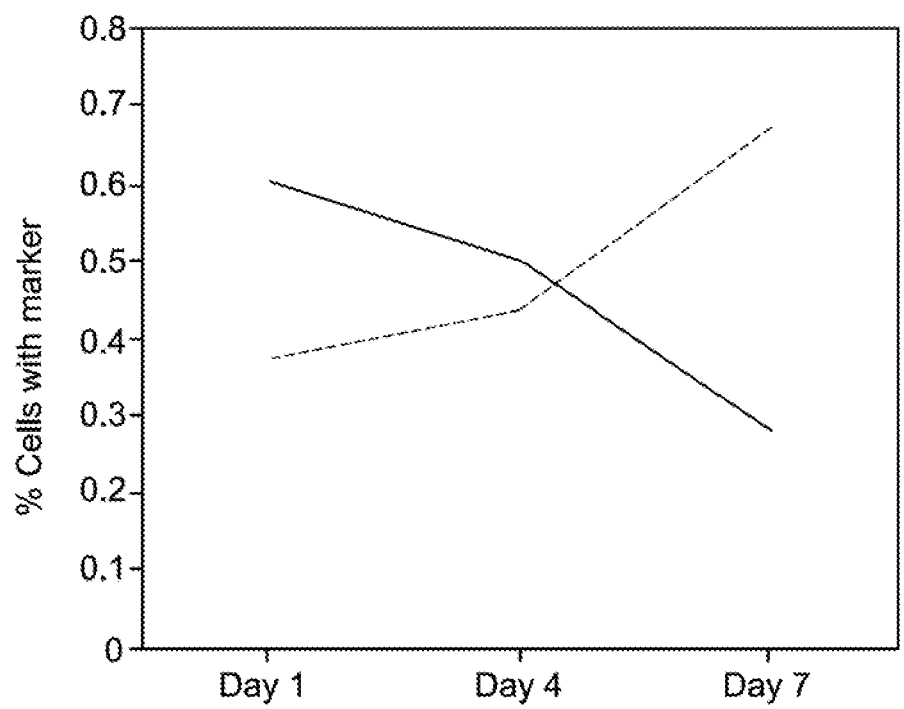

FIG. 13B shows the expansion of CD4 and CD8 T cells over a 7-day expansion period using DBTA [anti-CD3-o20b(+)act] in IL-2.

Figure 14:
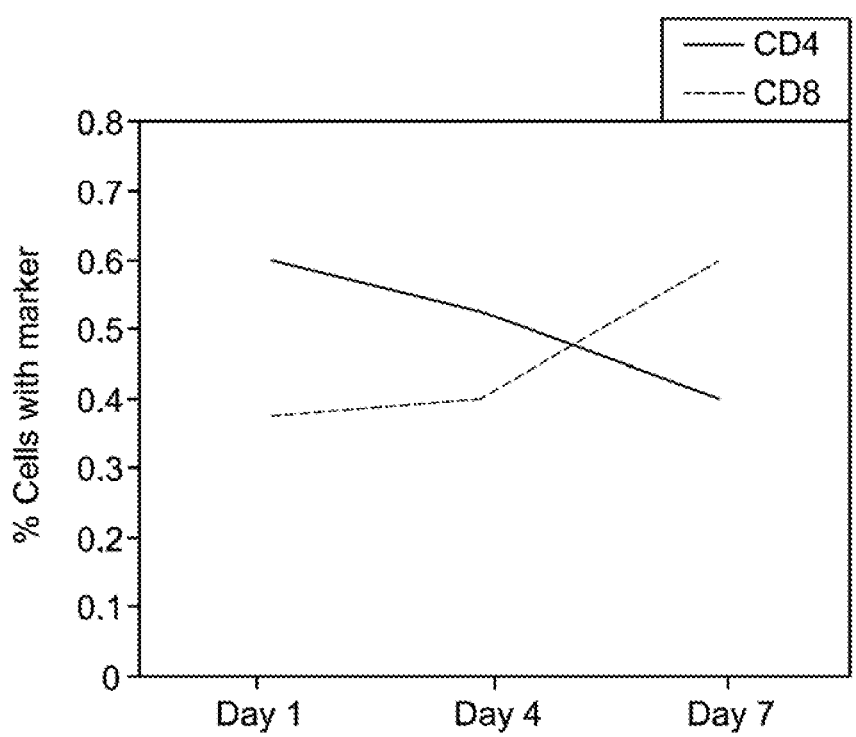

FIG. 14 shows the expansion of CD4 and CD8 T cells over a 7-day expansion period using DBTA [anti-CD3-o20b(+)act+anti-4-1BB-o20b(+)act].

Figure 15:
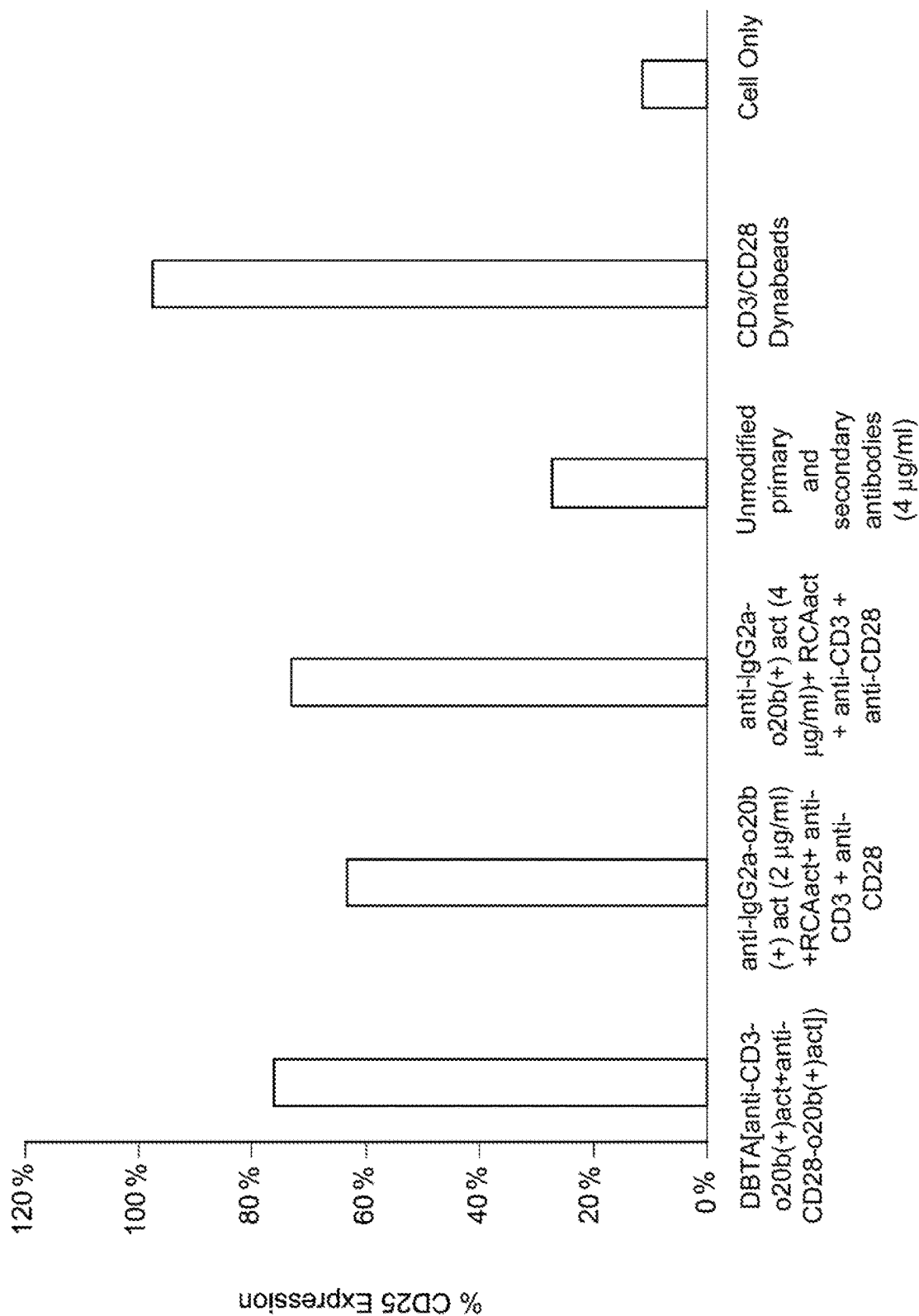

FIG. 15 shows the T cell activation (measured by CD25 expression) using a system comprising a first binder DNA sequence and/or second binder DNA sequence (o20b(+)act) attached to a secondary antibody (anti-IgG2a), unmodified anti-CD3 primary antibody and unmodified anti-CD28 primary antibody, and rolling circle amplification product (RCAact). The different conditions used were: i) anti-IgG2a-o20b(+)act) (2 μg/mL)+RCAact+unmodified anti-CD3+unmodified anti-CD28, in which the secondary antibody-DNA conjugate was at 2 μg/mL concentration, unmodified primary antibodies anti-CD3 and anti-CD28 were at 1 μg/mL concentration and RCAact was at 10-fold molar excess with respect to primary antibodies anti-CD3 and anti-CD28; and ii) anti-IgG2a-o20b(+)act) (4 μg/mL)+RCAact+unmodified anti-CD3+unmodified anti-CD28, in which the secondary antibody-DNA conjugate was at 4 μg/mL concentration, unmodified primary antibodies anti-CD3 and anti-CD28 were at 1 μg/mL concentration and RCAact was at 10-fold molar excess with respect to primary antibodies anti-CD3 and anti-CD28. DBTA[anti-CD3-o20b(+)act+anti-CD28-o20b(+)act] and a mixture of unmodified anti-CD3 (1 μg/mL), anti-CD28 (1 μg/mL) and IgG2-specific secondary (4 μg/mL) antibodies were used as controls. Dynabeads® Human T-Expander CD3/CD28 (denoted as CD3/CD28 Dynabeads) and cells only samples were used as additional controls.

FIG. 16 shows the NK cell activation (measured by CD25 expression) using a system comprising a first binder DNA sequence and/or second binder DNA sequence (o20b(+)act) attached to a secondary antibody (anti-IgG1), unmodified primary antibodies (anti-CD335 and anti-CD2, or anti-CD335 and anti-CD244), and rolling circle amplification product (RCAact). The different conditions used were: i) anti-IgG1-o20b(+)act)+RCAact+anti-CD335+anti-CD2; and ii) anti-IgG1-o20b(+)act)+RCAact+anti-CD335+anti-CD244. Cells only, and soluble antibodies only samples were used as negative controls.

DETAILED DESCRIPTION

Practice of the invention will be still more fully understood from the following examples, which are presented herein for illustration purposes only and should not be construed as limiting the scope of the present invention as defined by the appended claims. Some abbreviations used in the examples section are expanded as follows: "mg": milligrams; "ng": nanograms; "pg": picograms; "fg": femtograms; "mL": milliliters; "mg/mL": milligrams per milliliter; "mM": millimolar; "mmol": millimoles; "pM": picomolar; "pmol": picomoles; "μL": microliters; "min.": minutes and "h.": hours.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least each numerical parameter should at least be construed in light of the number of reported significant digits and by applying ordinary rounding techniques.

Some embodiments are directed towards a method of activating immune cells. The method includes providing a population of immune cells and contacting the population of immune cells with a first agent and a second agent. The first agent includes an immune cell activator attached to a first binder moiety, and the second agent includes at least one capture oligomer. The at least one capture oligomer is capable of associating with the first binder moiety.

While certain embodiments are directed towards autologous cell therapies that involve collection, manipulation, and re-insertion of a patient's own cells, the applications of the disclosed techniques may include allogenic cells. The applications may also include modified human cells, immortalized cell lines (e.g., NK92 cell lines), or non-human cells. Cell based therapies that are contemplated as being used in conjunction with the disclosed techniques include, but not limited to, therapies for organ or tissue regeneration, cancer treatment, blood disorders, immunotherapies, heart disease, or any other cell-based therapies. A variety of cell types may be utilized within the context of the present invention including for example, but not limited to, immune cell types such as B cells, T cells (including tumor infiltrating lymphocytes), or natural killer cells. The cells can be isolated from any tissue such as peripheral blood, bone marrow, or tumor tissue. Some embodiments are directed towards T cells enriched from peripheral blood. Enrichment may be performed by centrifugation using, for example, Ficoll-Paque™ or Percoll™ gradient (GE Healthcare). Some other embodiments are directed towards a specific subpopulation of T cells, such as CD28+, CD4+, CD8+, CD45RA+, and/or CD45RO+ T cells. The cells may be isolated by positive or negative selection techniques.

As used herein, the term "first agent" refers to a component that is capable of associating with a "second agent" and activating an activatable cell such as immune cell. The first agent includes a cell activator attached to a "first binder moiety". The first binder moiety is a molecule that is capable of associating with the "second agent". The second agent refers to a capture polymer comprising at least one capture oligomer, wherein the at least one capture oligomer is capable of associating with the first binder moiety. Thus, the first agent is capable of associating with the second agent via the first binder moiety.

As used herein, the term "immune cell activator" refers to any agent that can activate cells of the adaptive or innate immune system (e.g. T cells or natural killer cells) for proliferation, enhanced cytotoxic potential, and/or transduction.

The term "attached" refers to any means of attachment known in the art. The attachment may be a covalent linkage or a non-covalent interaction (e.g., an electrostatic, or a hydrophobic interaction). A non-covalent interaction is also referred to as "association".

As used herein, the term "in situ" generally refers to an event occurring in the original location. In situ, may refer to an event occurring in a medium containing a population of immune cells such as the medium where immune cell activation occurs. In some embodiments "in situ" refers to an event happening in the immune cell culture medium under cell culturing condition.

In some embodiments, the cell activator is an immune cell activator and the first binder moiety is a first binder nucleic acid sequence. Thus, the first agent includes an immune cell activator attached to the first binder nucleic acid sequence. In such embodiments, the second agent comprises at least one "capture oligomer" that is capable of associating (i.e., via non-covalent interaction) with the first binder nucleic acid sequence. In some embodiments, the second agent is a capture nucleic acid polymer and the capture oligomer is a "capture oligonucleotide". In some embodiments, the capture nucleic acid polymer comprises a single capture oligonucleotide. In some embodiments, the capture nucleic acid polymer comprises a plurality of capture oligonucleotides. The capture oligonucleotides in the plurality of capture oligonucleotides may all be of the same type (i.e., all capture oligonucleotides have the same nucleotide sequence) or different types (i.e., each capture oligonucleotide has different nucleotide sequence, or a first set of capture oligonucleotide has a different nucleotide sequence as compared to a second set), with the proviso that at least one capture oligonucleotide is capable of associating with the first binder nucleic acid sequence. In some embodiments, the second agent is a rolling circle amplification product. The rolling circle amplification product may be made by amplifying a circular nucleic acid template by rolling circle amplification to form a concatemer, wherein the concatemer comprises repeat units of the circular nucleic acid template sequence. A rolling circle amplification product comprising capture oligonucleotides of the same type or different types can be generated by appropriate designing of the nucleic acid template sequence. For example, a rolling circle amplification product comprising capture oligonucleotides of different types may be made by tailoring the template nucleic acid sequence to contain the sequences of interest. Also, by manipulating the circular template and by using multiple primers, the rolling circle amplification products can be tailor-designed to yield complex structures. In some embodiments, the plurality of capture oligonucleotides in the capture nucleic acid polymer include tandem repeats of the same nucleotide sequence. In some embodiments, capture nucleic acid polymer comprises at least two capture oligonucleotides, wherein at least one capture oligonucleotide is capable of associating with the first binder nucleic acid sequence, and wherein at least one other capture oligonucleotide is capable of associating with a second binder nucleic acid sequence. In some embodiments, the number of capture oligonucleotides in the capture nucleic acid polymer is greater than 3, preferably greater than 30, and more preferably greater than 300. In certain embodiments, the number of capture oligonucleotides is greater than 2000. As such, the capture nucleic acid polymer may comprise a plurality of capture oligonucleotides of the same or different nucleotide sequence, molecular weights, geometrical arrangements, and/or patterns of repetition. In some embodiments, the capture oligonucleotide may have a length in range of from about 6 nucleotides to about 12 nucleotides, from about 12 nucleotides to about 25 nucleotides, from about 25 nucleotides to about 50 nucleotides, from about 50 nucleotides to about 100 nucleotides, from about 100 nucleotides to about 250 nucleotides, or from about 250 nucleotides to about 500 nucleotides. In some embodiments, the second agent is a double-stranded capture nucleic acid polymer while in other embodiments it is a single-stranded capture nucleic acid polymer. The capture nucleic acid polymer may include natural or unnatural nucleotides with modifications on the nucleic acid base, sugar or phosphate backbone. The second agent may further comprise spacer oligonucleotide sequences having different number and/or sequence of nucleotides than the capture oligonucleotide, or non-nucleic acid spacer molecules.

The first binder nucleic acid sequence is complementary to the at least one capture oligonucleotide. The first binder nucleic acid sequence and the at least one capture oligonucleotide are capable of associating via complementary base-pair hybridization. In some embodiments, all the nucleotide residues of the at least one capture oligonucleotide may hybridize to complementary nucleotides in the first binder nucleic acid sequence. For example, the capture oligonucleotide may have 50 nucleotide residues and all the 50 nucleotide residues may hybridize to complementary nucleotides in the first binder nucleic acid sequence. In some embodiments, all the nucleotides of the capture oligonucleotide may not have corresponding complementary nucleotides in the first binder nucleic acid sequence. In some embodiments, there may be one or more base-pair mismatches between the capture oligonucleotide and the first binder nucleic acid sequence. In still other embodiments, the capture oligonucleotide and/or the first binder nucleic acid sequence may include nucleic acid analogs, with modified bases such as azidothymidine, inosine, or uridine, or modified sugars (e.g. 2'-O-alkyl modified furanoside), or modified backbones (e.g. phosphorothioate, alkylphosphonate, phosphoramidate backbones).

In some other embodiments, the second agent is a cationic capture polymer comprising at least one cationic capture oligomer, containing contiguous stretches of cationic monomers such as histidine or lysine. In some embodiments, the cationic capture polymer comprises a plurality of cationic capture oligomers. The cationic capture polymer may further comprise neutral or anionic spacer residues provided that the overall charge remains cationic.

The first or second agent may further comprise non-complementary spacer nucleotide sequences or non-nucleic acid spacer molecules. In some embodiments, the first binder moiety is an anionic first binder moiety such as a first binder nucleic acid sequence, alginate, polyglutamate, polyaspartate or hyaluronate and the second agent is a cationic capture polymer comprising at least one cationic capture oligomer. The anionic first binder moiety is capable of associating with the at least one cationic capture oligomer via electrostatic association. In still other embodiments, the first binder moiety is a cationic first binder moiety and the second agent is an anionic capture polymer comprising at least one anionic capture oligomer.

In some embodiments, the immune cell activator is attached to the first binder moiety by a covalent linkage. The immune cell activator may be attached to the first binder moiety by any covalent linkage known in the art, such as thiol/maleimide or carbodiimide/amine attachment chemistries. In some embodiments, the immune cell activator is attached to the first binder moiety by a non-covalent interaction. In some other embodiments, the immune cell activator is attached to the first binder moiety by a non-covalent interaction via an intermediate binder moiety, wherein the intermediate binder moiety is attached (via covalent linkage or non-covalent interaction) to the first binder moiety. In some embodiments, the intermediate binder moiety is attached to the first binder moiety by a covalent linkage, and the intermediate binder moiety is capable of attaching with the immune cell activator by a non-covalent interaction. In some embodiments, the intermediate binder moiety is capable of directly attaching with the immune cell activator. For example, the intermediate binder moiety may be a secondary antibody and the immune cell activator may be a primary antibody. In general, secondary antibodies are directed against a species of the primary antibody. For example, when the immune cell activator is a mouse antibody, a suitable secondary antibody may be a polyclonal antibody with specificity for the mouse immunoglobulin, such as sheep or goat-derived anti-mouse polyclonal antibody or anti-mouse monoclonal antibody such as rat-derived anti-mouse Fc antibody. In some other embodiments, the intermediate binder moiety is capable of indirectly attaching with the immune cell activator via a linker moiety, wherein the linker moiety is covalently attached to the immune cell activator. For example, when the linker moiety is a biotin or a derivative thereof, a suitable intermediate binder moiety may be an avidin or an antibody specific for biotin. Alternatively, when the linker moiety is an avidin, a suitable intermediate binder moiety may be biotin or an anti-avidin antibody.

In some embodiments, the first binder moiety attached to the intermediate binder moiety and the immune cell activator are mixed prior to contacting a population of immune cells, to form a preformed or a pre-associated first agent. In such embodiments, the preformed or pre-associated first agent may then be added to the population of immune cells for activating the immune cells. In some other embodiments, a first binder moiety attached to the intermediate binder moiety and an immune cell activator are added separately to a population of immune cells contained in a medium, without prior mixing. In such embodiments, the first agent is formed in situ.

In some embodiments, the disclosure relates to a method of activating immune cells, the method comprising, providing a population of immune cells and contacting the population of immune cells with a first agent and a second agent. The first agent comprises an immune cell activator and a first binder nucleic acid sequence, wherein the immune cell activator is attached to the first binder nucleic acid sequence via an intermediate binder moiety. The intermediate binder moiety is attached to the first binder nucleic acid sequence by a covalent linkage, and the intermediate binder moiety is capable of attaching with the immune cell activator by a non-covalent interaction. The second agent comprises at least one capture oligomer, and the at least one capture oligomer is capable of associating with the first binder nucleic acid sequence. In some embodiments, the immune cell is a T cell or a NK cell.

In some embodiments, the immune cell activator may be a T cell activator. Suitable examples of T cell activator include, but not limited to, small organic molecules (e.g., ionomycin, phorbol myristate or acetate), natural or modified peptides, proteins (e.g., antibodies or affibodies), non-natural peptide mimics, nucleic acids (e.g., polynucleotides, PNA, DNA, RNA or aptamers), polysaccharides (e.g., lectins or sugars), lipids, enzymes, enzyme substrates or inhibitors, ligands, receptors, antigens, or haptens. A T cell activator may activate a T cell by binding to a T cell surface receptor, such as a T cell activating receptor, which results in delivery of a primary activation signal in a T cell. Examples of T cell activating receptors include, but not limited to, T cell Receptor (TCR) or CD3 receptor. A primary activation signal may be initiated through binding between a TCR and an antigen presented in conjunction with either MHC class I or class II molecules in order to stimulate an antigen-specific T cell activation. A primary activation signal may also be initiated through binding between a CD3 receptor and a ligand targeted to the CD3 receptor in order to stimulate a polyclonal T cell activation. In some example embodiments, the T cell activator is an anti-CD3 antibody or fragments thereof (e.g., the CD3 receptor binding fragments). Other examples of T cell activator include concanavalin A, protein kinase C (PKC) activator such as a phorbol ester (e.g., phorbol myristate acetate) or calcium ionophore (e.g., ionomycin which raises cytoplasmic calcium concentrations) and the like.

Some embodiments are directed to a method of activating T cells, the method comprising providing a population of T cells and contacting the population of T cells with a first agent and a second agent. The first agent includes a T cell activator attached to a first binder moiety, and the second agent includes at least one capture oligomer. The at least one capture oligomer is capable of associating with the first binder moiety. In some embodiments, the association between the at least one capture oligomer with the first binder moiety brings the T cell activators in proximity to each other, causing a clustering of the T cell surface receptors. In some embodiments, the T cell activator is an anti-CD3 antibody. In some embodiments, the first binder moiety is a first binder nucleic acid sequence and the second agent is a capture nucleic acid polymer comprising at least one capture oligonucleotide. In some embodiment, the capture nucleic acid polymer is a rolling circle amplification product. In some embodiments, the first binder moiety is a first binder nucleic acid sequence and the second agent is a cationic capture polymer.

In some embodiments, the method of activating the T cells include addition of multiple types of first agents. For example, in some embodiments, the method of activating T cells may include addition of first agents that include two different types of activators (e.g., anti-CD3 antibody and concanavalin A). For example, one type of first agent can include anti-CD3 antibody attached to a first binder nucleic acid sequence and the other type of first agent can include concanavalin A attached to a first binder nucleic acid sequence.

In some embodiments, the method of activating T cells further comprises the addition of a T cell co-stimulator. Examples of T cell co-stimulators include but are not limited to ligands targeted towards T cell co-stimulatory receptors such as CD28, CD2, ICOS, OX40, or 4-IBB receptors. In some embodiments, the method of activating T cells can include the addition of two different types of T cell co-stimulators (e.g., anti-CD28 antibody and anti-4-IBB antibody). In some embodiments, the T cell co-stimulator may be attached to a second binder moiety. In some embodiment, the second binder moiety is a second binder nucleic acid sequence. In such embodiments, second agent is a capture nucleic acid polymer comprising at least two capture oligonucleotides, wherein at least one capture oligonucleotide is capable of associating with the first binder nucleic acid sequence, and wherein at least one other capture oligonucleotide is capable of associating with the second binder nucleic acid sequence. In some embodiments, the first binder nucleic acid sequence and the second binder nucleic acid sequence have the same sequence of nucleotides. In such embodiments, both the capture oligonucleotides in the at least two capture oligonucleotides are identical and complementary to the first binder nucleic acid sequence and the second binder nucleic acid sequence. In some other embodiments, the first binder nucleic acid sequence and the second binder nucleic acid sequence are of different types and do not have the same sequence of nucleotides. In such embodiments, the capture oligonucleotides have different sequence of nucleotides, with the proviso that at least one capture oligonucleotide is complementary to the first binder nucleic acid sequence and the at least one other capture oligonucleotide is complementary to the second binder nucleic acid sequence. In some other embodiments, the second agent is a cationic capture polymer and the second binder moiety is an anionic second binder moiety. In still other embodiments the second agent is an anionic capture polymer and the second binder moiety is a cationic second binder moiety.

In some embodiments, the T cell activator is non-covalently attached to the first binder nucleic acid sequence via an intermediate binder moiety. Some embodiments are directed to a method of T cell activation, wherein the first agent is formed in situ. In such embodiments, the method comprises adding to a population of T cells, a T cell activator, a first binder nucleic acid sequence attached to an intermediate binder moiety, and a second agent comprising at least one capture oligomer and incubating the population of T cells to activate the T cells. The intermediate binder moiety is capable of attaching with the T cell activator, and the at least one capture oligomer is capable of associating with the first binder nucleic acid sequence.

In some embodiments, the T cell activator is a primary antibody, such as an anti-CD3 antibody and the intermediate binder moiety is a secondary antibody. The first binder nucleic acid sequence is attached to the secondary antibody via a covalent linkage and the secondary antibody is capable of attaching with the primary antibody by a non-covalent interaction.

Some embodiments are directed to a method of T cell activation, wherein the first agent, the second agent, and optionally the T cell co-stimulator, which may or may not be attached to a second binder moiety, are added simultaneously or sequentially in any order, to a population of T cells provided in a media, to allow an in situ association. In yet other embodiments, the first agent, the second agent, and optionally a T cell co-stimulator attached to a second binder moiety, are allowed to associate to form a pre-associated complex. The pre-associated complex is then added to the population of T cells. In preferred embodiments, the first agent, the second agent, and optionally the T cell co-stimulator attached to a second binder moiety, are allowed to associate in situ.

In some embodiments, the time sufficient to activate a portion of the population of immune cells, such as a T cell, may range from about 1 min to about 14 days. In certain embodiments, the time period may range from about 24 h to about 8 days. In some embodiments, at least 15% of T cells are activated. In preferred embodiments, at least 25% of the T cells are activated, and in more preferred embodiment, a majority of the T cells, greater than 50%, are activated. The incubation may be done in a bioreactor having a controlled environment of temperature, humidity, $CO_2$ concentration, for example, at 37° C. and 5% $CO_2$. In some embodiments, the incubation may be done in a static bioreactor where there is no movement of the bioreactor, while in some other embodiments the incubation may be done in a bioreactor placed on a rocking platform.

In some embodiments, the disclosure provides methods to activate and selectively expand a specific subpopulation of T cells from a mixed population of T cells. This can be achieved, for example, by varying the nature or relative proportion of the T cell activators and T cell co-stimulators. Further, the disclosure provides methods to control T cell surface receptor clustering and hence activation by adjusting, for example, the number of or distance among the T cell activators and T cell co-stimulators, which are associated with the second agent. In an example, where the second agent is a capture nucleic acid polymer, this can be achieved by controlling the number and/or length of the capture oligonucleotides, and/or the length of the spacers. The level of cell activation can also be controlled by controlling the association between the first agent and the second agent, which can be done, for example, by varying the number of first binder moieties attached to the T cell activator. In some embodiments, the relative population of CD4 and CD8 T cells can be modulated by changing the nature or relative proportion of the T cell activators and T cell co-stimulators. For example, the proportion of CD8 cells can be increased over CD4 cells by changing the T cell co-stimulator from an antibody directed towards the CD28 receptor to an antibody directed towards the 4-1BB receptor.

Any method known in the art can be used to assess the activation of the immune cells. In some embodiments, the expression of certain antibodies such as CD25 may be used to measure the activation of the T cells. In certain embodiments, the expression of CD25 receptors on the T cells may be assayed by labeled anti-CD25 antibodies to enumerate the labeled cells. In certain other embodiments, activation, expansion of T cell subtypes, and differentiation may be measured by other markers. The other markers used to measure T cell activation, expansion, and/or differentiation include, but not limited to, CD4, CD8, CD27, CD28, CD3, CD57, CD25, CD45RA, CD45RO, CD127, and CD62L.

Some embodiments are directed to a method of activating NK cells, the method comprising providing a population of natural killer cells and contacting the population of natural killer cell with a first agent and a second agent. The first agent includes a NK cell activator attached to a first binder moiety, and the second agent includes at least one capture oligomer. The at least one capture oligomer is capable of associating with the first binder moiety. In some embodiments, the NK cell activator is attached to the first binder moiety via an intermediate binder moiety. In some embodiments, the first binder moiety is a first binder nucleic acid sequence.

Some embodiments are directed to a method of NK cell activation, wherein the first agent is formed in situ. In such embodiments, the method comprises adding to a population of NK cells, a natural killer cell activator, a first binder nucleic acid sequence attached to an intermediate binder moiety, and a second agent comprising at least one capture oligomer and incubating the population of NK cells to activate the NK cells. The intermediate binder moiety is capable of attaching with the natural killer cell activator, and the at least one capture oligomer is capable of associating with the first binder nucleic acid sequence.

In some embodiments, the immune cell activator may be a natural killer cell activator. Suitable examples of natural killer cell activator include ligands targeted towards activating receptors including but not limited to, NKG2D receptor, the signaling lymphocytic activation molecule (SLAM) family receptors such as CD244 (2B4), the DNAX accessory molecules such as CD226, the natural cytotoxicity receptors (NCRs) such as NKp30, NKp44, NKp46 (CD335), or NKp80, the tumor necrosis factor receptor superfamily such as CD137 (4-1BB), CD134 (OX40), or CD27, or the cytokine receptors such as Il-2R, Il-15R, Il-18R, or Il-21R. Suitable examples of natural killer cell activators include but are not limited to small organic molecules, natural or modified peptides, proteins (e.g., antibodies or affibodies), non-natural peptide mimics, nucleic acids (e.g., polynucleotides, PNA, DNA, RNA or aptamers), polysaccharides (e.g., lectins or sugars), or lipids.

In some embodiments, the method of activating NK cells includes addition of first agents that include two different types of natural killer cell activators (e.g., anti-CD335 antibody and anti-CD244 antibody). For example, one type of first agent may include an anti-CD335 antibody attached to a first binder nucleic acid sequence and the other type of first agent may include an anti-CD244 antibody attached to another first binder nucleic acid sequence. In yet another example, one type of first agent may include an anti-CD335 antibody attached to a first binder nucleic acid sequence and the other type of first agent may include an anti-CD2 antibody attached to another first binder nucleic acid sequence.

Some embodiments are directed to a method of activating immune cells, the method comprising providing a population of immune cells and contacting the population of immune cells with a first agent and a second agent, wherein the first agent and the second agent are soluble in any media suitable for placing cells. As to be understood, a media suitable for placing cells may include any isotonic media including a cell culture media. In some embodiments, the cell culture media may include any immune cell culture media that are known in the art such as a T cell culture media. Illustrative cell culture media include, but are not limited to, RPMI 1640, AIM-V, DMEM, MEM, α-MEM, F-12, X-Vivo 15, CellGRO™ SCGM. The cell culture media may be serum-free or supplemented with serum, such as human serum or serum supplement. In some embodiments, the cell culture media is further supplemented with additional growth factors and cytokines such as interleukin-2 (Il-2), interleukin-7 (Il-7) or interleukin-15 (IL-15).

In some embodiments, the first agent and the second agents are bio-degradable. In some embodiments, the degradation may occur by chemical or enzymatic means. In some embodiments, where the second agent is a capture nucleic acid polymer and/or the first binder moiety is a first binder nucleic acid sequence, the first binder moiety and the second agent may be removed without affecting the T cells by the addition of a nuclease. In some embodiments, the nuclease, is added after at least a portion of the population of T cells are activated. In some embodiments, the degrading enzyme is added after the T cells have expanded at least 10-100 fold. In yet other embodiments, the nuclease is added at the end of the culture period, before the T cells are harvested from the cell culture media, prior to washing, concentration and making the final formulation. It should be noted that the nuclease can be added any time after at least a portion of the population of T cells is activated and before the T cells are administered into a patient. In certain embodiments, after degradation, the degraded by-products of the first and second agents may be removed during washing and concentration of the T cells, and additional purification steps are not necessary. In some other embodiments, the second agent and the first agent are biocompatible and may be rapidly degraded in the blood stream. In such cases, the addition of a degrading enzyme may not be required before the T cells are administered into a patient. The use of such soluble, biodegradable systems are advantageous over polystyrene beads or other comparable bead based approaches since the use of such soluble, biodegradable systems may avoid the need for additional purification steps, such as magnetic separation, which often leads to significant cell loss. In embodiments that include the addition of a T cell co-stimulator attached to a second binder moiety, the second binder moiety may also be biodegradable.

In some embodiments, the method of immune cell activation further comprises addition of a vector comprising a foreign gene. For example, the method of T cell activation further includes the addition of a vector carrying a foreign gene, which encodes a chimeric antigen receptor or a T cell receptor. In some embodiments, the vector is a viral vector such as a γ-retroviral vector or a lentiviral vector. In some other embodiments, the vector is a plasmid vector. In some embodiments, the vector is added simultaneously with the first agent, while in some other embodiments, the vector is added after at least a portion of the population of immune cells is activated.

Some embodiments are directed towards a kit comprising an immune cell activator attached to a first binder nucleic acid sequence and a capture nucleic acid polymer comprising at least one capture oligonucleotide, wherein the at least one capture oligonucleotide is complementary to the first binder nucleic acid sequence. In some embodiments, the capture nucleic acid polymer is a rolling circle amplification product. In some embodiments, the immune cell activator is attached to the first binder nucleic acid sequence via an intermediate binder moiety.

Some embodiments are directed towards a kit comprising, an immune cell activator, a first binder nucleic acid sequence covalently attached to an intermediate binder moiety, and a second agent comprising at least one capture oligomer. The intermediate binder moiety is capable of attaching with the immune cell activator and the at least one capture oligomer is capable of associating with the first binder nucleic acid sequence. In some embodiments, the second agent is a capture nucleic acid sequence such as a rolling circle amplification product. In some embodiments, the immune cell activator is a natural killer cell activator such as an anti-CD335 antibody, an anti-CD244 antibody, anti-CD2 antibody or combinations thereof.

Some embodiments are directed towards a kit comprising an intermediate binder moiety covalently attached to a first binder nucleic acid sequence and a capture nucleic acid polymer comprising at least one capture oligonucleotide. The intermediate binder moiety is capable of attaching with an immune cell activator and the at least one capture oligonucleotide is capable of associating with the first binder nucleic acid sequence. In some embodiments, the intermediate binder moiety is a secondary antibody and the immune cell activator is a primary antibody. In some embodiments, the immune cell activator is a natural killer cell activator such as an anti-CD335 antibody, an anti-CD244 antibody, anti-CD2 antibody or combinations thereof. In some other embodiments, the immune cell activator is a T cell activator such as an anti-CD3 antibody.

Some embodiments are directed towards a kit comprising a T cell activator attached to a first binder nucleic acid sequence and a capture nucleic acid polymer comprising a plurality of capture oligonucleotides. In some embodiments, the kit further comprises a T cell co-stimulator. In some embodiments, the T cell co-stimulator is attached to a second binder nucleic acid sequence. In some embodiments, the capture nucleic acid polymer is a capture DNA polymer, the first binder nucleic acid sequence is a first binder DNA sequence and the second binder nucleic acid sequence is a second binder DNA sequence. In specific examples the kit is a DNA-Based T cell Activation (DBTA) composition comprising a capture DNA polymer such as a rolling circle amplification product and a T cell activator such as an anti-CD3 antibody attached to a first binder DNA sequence. In some examples, the DBTA composition further comprises a T cell co-stimulator such as an anti-CD28 antibody or an anti-41BB antibody. In some examples the T cell co-stimulator is attached to a second binder DNA sequence.

EXAMPLES

DNA-Based T cell Activation (DBTA) compositions are representative capture nucleic acid polymer containing systems that initiate T cell clustering, activation, and subsequent expansion. Some of the possible DBTA compositions are: A) a capture DNA polymer and a T cell activator attached to a first binder DNA sequence; or B) a capture DNA polymer, a T cell activator attached to a first binder DNA sequence, and a T cell co-stimulator; or C) a capture DNA polymer, a T cell activator attached to a first binder DNA sequence, and a T cell co-stimulator attached to a second binder DNA sequence. In examples where the T cell activator is an antibody and/or the T cell co-stimulator is an antibody, a T cell activator attached to a first binder DNA sequence and/or T cell co-stimulator attached to a second binder DNA sequence have been generically referred to as "antibody-DNA conjugate" or "Ab-DNA".

Example 1: Synthesis of Antibody-DNA (Ab-DNA) Conjugates & Generation of Various DBTA Compositions One of the DBTA compositions includes a capture DNA polymer such as a rolling circle amplification product derived from human beta-actin (RCAact) comprising tandem repeats of 43-base oligonucleotide segments and the following components: (1) anti-human CD3 monoclonal antibody (anti-CD3, T cell activator) covalently attached to 20-base DNA sequence derived from human beta-actin (o20b(+)act) (SEQ ID No. 4, first binder DNA sequence), and (2) anti-human CD28 monoclonal antibody (anti-CD28) covalently attached to 20-base DNA sequence also derived from human beta-actin (o20b(+)act) (SEQ ID NO. 4, a second binder DNA sequence). Such a DBTA composition is denoted as "DBTA[anti-CD3-o20b(+)act+anti-CD28-o20b(+)act]". One another DBTA composition includes the rolling circle amplification product (RCAact) and the following components: (1) anti-CD3 covalently attached to a 20-base DNA sequence derived from human beta-actin (o20b(+)act) (SEQ ID No. 4, first binder DNA sequence), and (2) anti-CD28. Such a DBTA composition is denoted as "DBTA[anti-CD3-o20b(+)act+unmodified anti-CD28]". The sequences of RCA template and primer for generating the rolling circle amplification product RCAact, and the corresponding first binder DNA sequence, and the second binder DNA sequence are given below in Table 1:

TABLE 1

Sequences for the first binder DNA sequence, the second binder DNA sequence, and the RCA template and primer for generating rolling circle amplification product, RCAact

| Name | sense | Length (5'→3') (bases including (b)) | Sequence modifications | Use/application |
|---|---|---|---|---|
| RCA primer (SEQ ID NO. 1) | − | 20 | TGA CTA TTA AGA CTT CCT GT | primer for RCA reactions, sequence derived from human beta-actin |
| RCA template (CpG) (SEQ ID NO. 2) | + | 43 | /Phos/TTA ATA GTC ATT CCA AAT ATG AGA TGC GTT GTT ACA GGA AGT C | template for RCA reactions, sequence derived from human beta-actin and contains CpG island |
| RCA template (no-CpG) (SEQ ID NO. 3) | + | 43 | /Phos/TTA ATA GTC ATT CCA ACA TAT GAG ATG GTT GTT ACA GGA AGT C | template for RCA reactions, sequence derived from humandoes not beta-actin and contain CpG island |

TABLE 1 -continued

Sequences for the first binder DNA sequence, the second binder DNA sequence, and the RCA template and primer for generating rolling circle amplification product, RCAact

| Name | sense | Sequence Length (5'→3') (bases including (b)) | modifications | Use/application |
|---|---|---|---|---|
| o20b(+) act (SEQ ID NO. 4) | + | 20 | /MalC6/ACA GGA AGT CTT AAT AGT CA | conjugation to Ab via 5'-maleimide and binding to human B-actin-derived RCA product |

Modification key:
Phos = 5' phosphate,
Mal = maleimide functional group,
C6 = hexylamino modification Synthesis of Conjugates of Anti-CD3-DNA and Anti-CD28-DNA The covalent attachment of the first binder DNA sequence and the second binder DNA sequence to anti-CD3 and anti-CD28 antibodies (Abs) respectively proceeds via a maleimide-thiol coupling strategy as described below. The following specific description of anti-CD3-o20b(+)act (anti-CD3-DNA) and anti-CD28-o20b(+)act (anti-CD28-DNA) conjugate synthesis, purification, and characterization can be adapted as a general conjugation strategy for different antibody (Ab) clones as well as different first and second binder nucleic acid sequences of different length and composition.

Preparation of Maleimide-Activated First Binder DNA Sequence and Second Binder DNA Sequence In this example, the first binder DNA sequence and the second binder DNA sequence have the same sequence of nucleotides. The process has been described for the first binder DNA sequence, but it also applies to the second binder DNA sequence. The starting DNA sequence (prot-mal-o20b(+)act) (TriLink Biotechnologies, San Diego, Calif., USA) includes a 20-base first binder DNA sequence capped with an N-terminal C6 spacer followed by a protected tricyclic maleimide moiety (prot-mal). A reactive maleimide-activated derivative (mal-o20b(+)act) was generated from prot-mal-o20b(+)act via an inverse electron-demand Diels-Alder deprotection step. The maleimide-activated first binder DNA sequence (mal-o20b(+)act) was suspended in anhydrous toluene (~1 mg/mL) and heated at 90° C. for 4 h. The maleimide-activated first binder DNA sequence (mal-o20b(+)act) was precipitated using benchtop centrifugation and solvent was removed. The precipitated mal-o20b(+)act was washed (3×1 mL) with cold ethanol. Upon further reduction of residual organic solvents under reduced pressure, the washed solid product was dissolved in 100 mM HEPES buffer, pH 7.3. The final concentration of mal-o20b(+)act was determined via UV-Vis spectroscopy (NanoDrop™ Spectrophotometer, Thermo Fisher Scientific, Waltam, Mass., USA). The resulting stock solution (0.5-1 mM in DNA) was used directly for antibody conjugation with a thiol-modified antibody. The remaining mal-o20b(+) act stock was stored for several months at −20° C. without significant loss of reactivity.

Preparation of Thiol-Modified Antibody Intermediates.

A 10 mM stock solution of Traut's reagent (2-iminothiolane hydrochloride) was first prepared in 100 mM HEPES buffer, pH 7.3. A 1 mg/mL solution of anti-CD3 Ab (OKT3 clone, eBioscience, Thermo Fisher Scientific, Waltam, Mass., USA) or anti-CD28 Ab (9.3 clone, GeneTex, USA) in PBS was then mixed with both 20×pH 8.5 borate buffer (Thermo Fisher Scientific, Waltam, Mass., USA) and 10-15 mM Traut's reagent stock solution in a 8:1:1 ratio by volume. The resulting solution was thoroughly mixed and allowed to incubate at room temperature for 0.75-1.25 h. The unused portion of the Traut's mixture may be stored for several months at −20° C. without major loss of reactivity, however a fresh solution is preferred. Following antibody activation, the reaction mixture was purified using a conventional desalting column (e.g. NAP-5 or PD-10, GE Healthcare Life Sciences) that has been equilibrated with 100 mM HEPES, pH 7.3 buffer. The collected fractions were then immediately analyzed by UV-Vis spectroscopy (NanoDrop™ Spectrophotometer, Thermo Fisher Scientific, Waltam, Mass., USA). The resulting protein recovery at this stage was typically >60% for both anti-CD3 and anti-CD28 antibodies measured using known molar extinction coefficients for antibody at 280 nm.

Conjugation of maleimide-activated DNA sequences (first binder DNA sequence and second binder DNA sequence) with thiol-modified Ab intermediates to generate Ab-DNA conjugates (anti-CD3-o20b(+)act and anti-CD28-o20b(+) act)

For the generation of antibody-DNA conjugate, a volume of mal-o20b(+)act was added to an aliquot of freshly prepared, purified, thiol-activated antibodies to achieve a target molar input ratio of 10-40:1 o20b(+)act:Ab. After thorough mixing, the resulting solution was allowed to incubate at 25° C. overnight (16-24 h). Final conjugate purification is achieved via selective precipitation of Ab using a saturated ammonium chloride solution. First, a volume of saturated ammonium chloride equal to the total reaction volume was added, thoroughly mixed, and placed on ice. After 15 mM, the sample was centrifuged at 15,000×g relative centrifugal force (rcf) for 10 mM at 10° C. Removal of the supernatant was followed by addition of an appropriate minimum volume of 0.1M sodium phosphate, 0.15M NaCl, pH 7 buffer to re-dissolve the final pellet. The final recovery and labeling efficiency of the antibody-DNA conjugate (Ab-DNA) was determined using the Pierce BCA Protein Assay Kit (Thermo Scientific, Waltam, Mass., USA) in combination with A260 measurement (NanoDrop™ Spectrophotometer, Thermo Fisher Scientific, Waltam, Mass., USA) for determination of DNA content ($\epsilon$=210,100 $M^{-1}$ $cm^{-1}$). Under these conditions, one to five first binder DNA sequences may be attached to each molecule of anti-CD3 antibody and/or one to five second binder DNA sequences may be attached to each molecule of anti-CD28 antibody. Attachment is generally achieved with a final conjugate recovery of >60%. Alternatively, antibody-DNA conjugate labeling and yield can also be measured by the method described in the supplementary material of reference Anal Chem. 2014 Apr. 15; 86(8): 3869-3875. Further confirmation of conjugate purity is determined using analytical size exclusion chromatography (SEC) against a standard protein size calibration curve. Typical analytical SEC conditions are as follows: 10 μL sample injection volume, 0.5 mL/min flow rate, 30 mM run using 100 mM sodium phosphate, 100 mM sodium sulfate, 0.05% sodium azide, pH 6.7 buffer on a TSK Gel 3000SWxL column (TOSOH Bioscience, Tokyo, Japan). Typical analytical SEC elution times are as follows: Unlabeled Ab=16.8-17.0 mM, unattached o20b(+)act=20.0 min, Ab-DNA (Ab-o20b(+)act) conjugate mixture=10-15 mM. Purified final Ab-DNA conjugates (after precipitation and resuspension) show >95% removal of unbound DNA intermediate or starting material upon SEC analysis.

Example 2: Validation of T Cell Binding for Anti-CD3-DNA and Anti-CD28-DNA Conjugates To ensure that the Ab-DNA conjugates prepared in Example 1 retain their specific cell binding capabilities to T cells, validation studies were performed for each conjugate batch using flow cytometry (Cytoflex S, Beckman Coulter). Normal Peripheral Blood (NPB) Pan T Cells (AllCells, USA) are thawed at 37° C. in 10 mL warm complete X-vivo media (see, Table 2) and then centrifuged at 300×g rcf for 10 min. The cells were then resuspended in 10 mL fresh complete media and analyzed on a Nucleocounter® NC-200 system to determine cell counts and viability. After adjusting the concentration to $1\times10^6$ cells/mL and washing with PBS, the T cells were blocked in 10% Normal Goat Serum (NGS) in PBS at 4° C. for 15 mM After removal of the blocking solution, the cells were incubated with antibodies and antibody-DNA conjugates in 1% NGS/PBS solutions for 15 mM at 4° C. In parallel experiments, cells were incubated with either anti-CD3-DNA (anti-CD3-o20b(+)act), or anti-CD28-DNA (anti-CD28-o20b(+)act). Cells incubated with unattached or unmodified anti-CD3 and anti-CD28 Ab were used as positive controls. After incubation, the cells were washed in PBS and incubated with a 1% NGS/PBS solution of fluorophore-labeled secondary antibody (Jackson ImmunoResearch, PA, USA) specific for the mouse isotype of both anti-CD3 and anti-CD28 Abs. Typical dilutions for secondary antibody labeling are 1:200 of a 1 mg/mL stock solution. After 15 min incubation at 4° C., the cells were washed as before, resuspended in PBS and analyzed by flow cytometry to determine the percentage of T cells bound with Ab-DNA conjugate relative to the percentage of T cells bound with unlabeled Ab (positive control).

FIGS. 1A through 1E show representative flow cytometry histograms for T cell binding by anti-CD28-o20b(+)act, anti-CD28 Ab (unlabeled), anti-CD3-o20b(+)act, anti-CD3 Ab (unlabeled), and FITC-labeled secondary antibody respectively. For these particular Ab-DNA conjugate batches (anti-CD28-o20b(+)act and anti-CD3-o20b(+)act), higher percentage of anti-CD3 and anti-CD28 cell binding was observed (>85% for both). These results indicate that despite DNA attachment, a significant portion of the anti-CD3 Ab and anti-CD28 Ab samples retain their T cell binding capabilities.

Figure 1A:
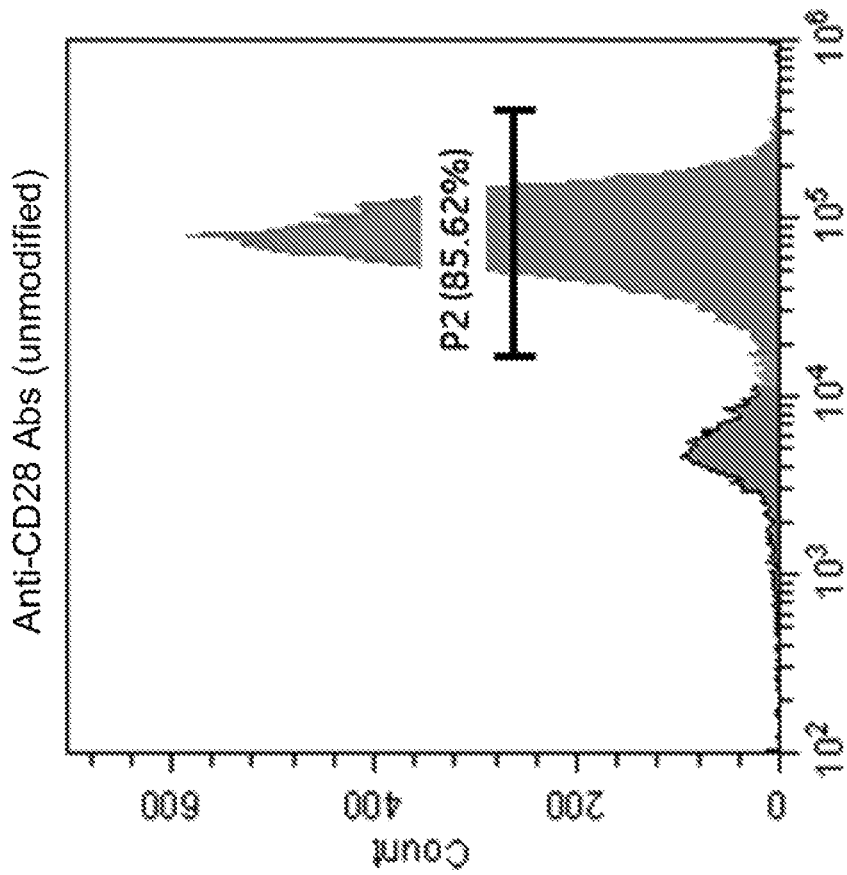
Figure 1B:
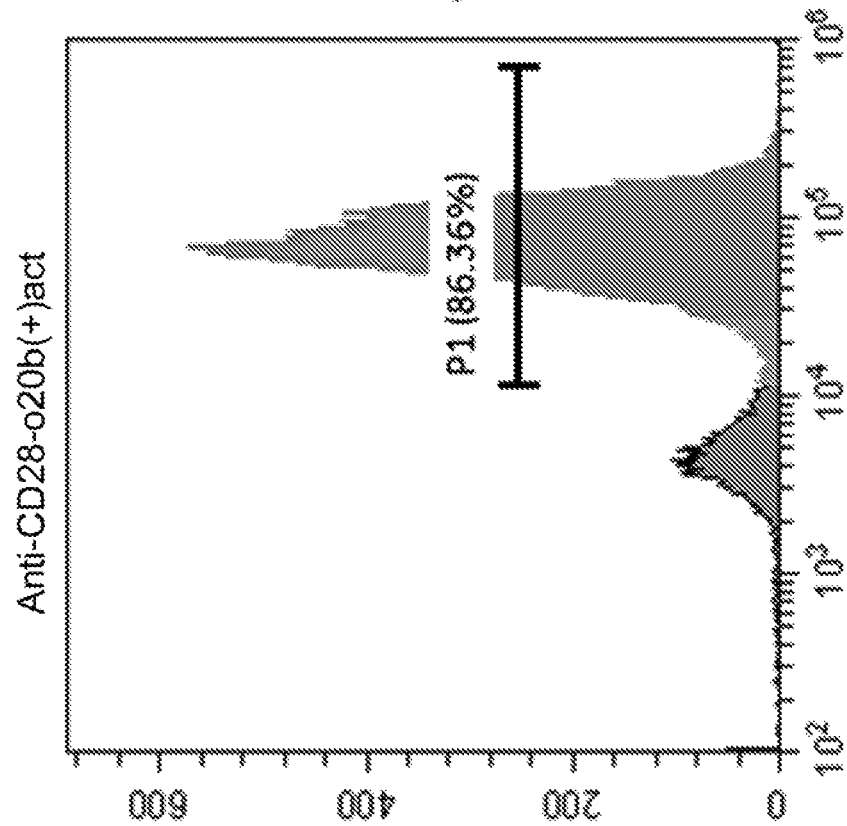
Figure 2:
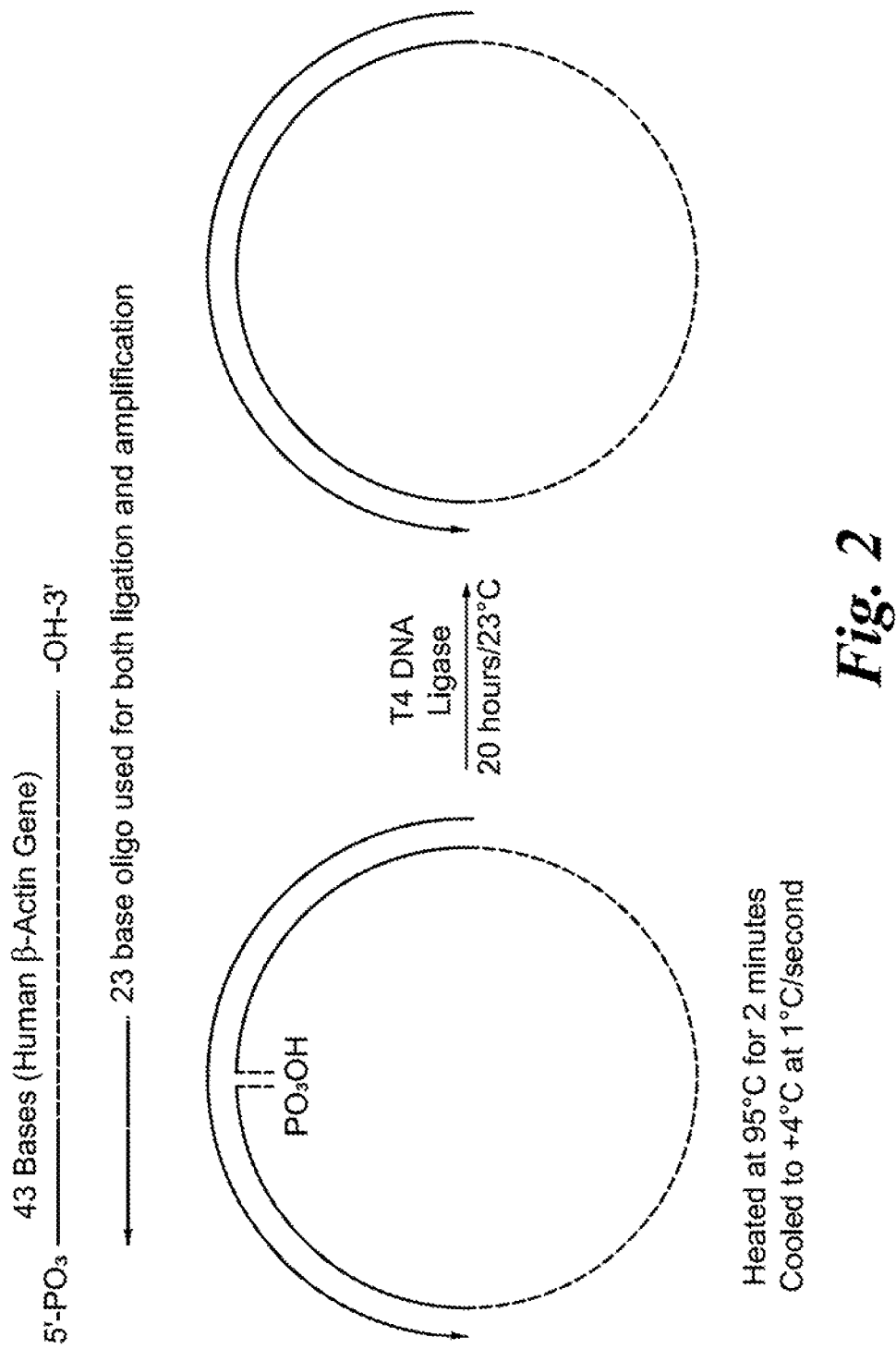

Example 3: Production of a Capture Nucleic Acid Polymer for T Cell Activation Using Rolling Circle Amplification The process of single-stranded rolling circle amplification (ssRCA) to produce rolling circle amplification product (e.g., RCAact) as a second agent for T cell activation comprises two steps: 1) ligation of a linear DNA strand to generate a circular template, and 2) amplification of the ligated circle to synthesize single stranded concatemers. The ligation was accomplished using T4 DNA Ligase following the manufacturer's protocol (New England Biolabs®, MA, USA). Two oligonucleotides were present in the ligation. One oligonucleotide (RCAact no-CpG, SEQ ID NO. 3) contained 43 bases of the nucleotide sequence of the human (3-actin gene and contained a 5' phosphate group. This 43-base oligonucleotide formed the circular template following ligation. The second oligonucleotide was 20 bases in length (RCAact Primer) and was complimentary to both ends of the 43-base oligonucleotide. This second oligonucleotide was used to both form the circle prior to ligation (template-dependent ligation of the 43-base oligonucleotide) and then amplify the circle in the subsequent ssRCA reaction (see, FIG. 2). For ligation, 450 pmol of the 43-base oligonucleotide were mixed in a 120 μL volume with 300 pmol of the 20 base oligonucleotide in an annealing buffer consisting of 10 mM Tris, pH 8, and 50 mM sodium chloride. The mixture was heated at 95° C. for two min and then cooled to +4° C. by dropping the temperature 0.1° C. every second. After cooling, the mixture was warmed to room temperature and 96 μL of this annealing reaction was mixed with 48 μL of 10×T4 DNA Ligase Buffer containing 10 mM ATP and 24 μl of T4 DNA Ligase (400 units/u1) in a final volume of 480 μL. The ligation reaction was allowed to incubate at 23° C. for 20 hours and then 65° C. for 20 mM to heat-kill the ligase.

The ssRCA reaction was performed by mixing 69.3 μL of the completed ligation reaction mixture with 550 μL of 2× Phi29 reaction buffer (100 mM HEPES Buffer, pH 8.0, 150 mM potassium chloride, 2 mM TCEP, 40 mM magnesium chloride, 0.02% (v/v) Tween 20, 5% (v/v) polyethylene glycol and 1.6 mM each dATP, dCTP, dGTP and dTTP) in a final volume of 1.078 mL. After mixing, 22 μL of 1 mg/ml Phi29 DNA polymerase was added to initiate rolling circle amplification. Amplification mixtures were incubated at 30° C. for 18 hours and then 65° C. for 15 min to heat-kill the polymerase. Completed ssRCA reaction mixtures were split equally into three separate tubes and precipitated by the addition of 0.1 volume 3M sodium acetate and 2.5 volumes of 95% (v/v) ethanol. Precipitations were allowed to stand at room temperature for 30 min and then centrifuged at high speed (>20,000×g) for 30 mM. The supernatants were removed by aspiration, each DNA pellet was rinsed with 500 μL of 70% (v/v) ethanol and then recentrifuged at high speed (>20,000×g) for 5 mM. The supernatants were again removed by aspiration and the DNA pellets re-suspended in TET Buffer (10 mM Tris, pH 8.0, 0.1 mM EDTA and 0.01% (v/v) Tween 20).

The apparent size of rolling circle amplification product (RCAact) was determined by pulse field gel electrophoresis relative to yeast (*S. cerevisiae*) or lambda DNA molecular weight ladders. Further, to confirm hybridization of anti-CD3-o20b(+)act and anti-CD28-o20b(+)act conjugates (Example 1) with RCAact, pulse-field analysis or gel-shift assays using non-denaturing agarose gels were used.

Example 4: Comparison of T Cell Activation and Expansion Using Dynabeads® Human T-Expander CD3/CD28 and DBTA Systems (DBTA[Anti-CD3-o20b(+)Act+Anti-CD28-o20b(+)Act] and DBTA [Anti-CD3-o20b(+)Act+Unmodified Anti-CD28])

Frozen aliquots of human Pan T Cells from AllCells (USA, Catalog #PB009-IF) were used for all activation and expansion studies. Pan T Cells were thawed and processed as described in Example 2 and added to following complete X-Vivo media (Lonza, Basel, Switzerland) to give an initial concentration of $1\times10^6$ cells/mL as shown in Table 2.

TABLE 2

Components of the complete X-Vivo media

| Component | Vendor | Catalogue Number | Final concentration in media | Volume (mL) |
|---|---|---|---|---|
| Human serum (off the clot) | Valley Biomedical (VA, USA) | HS1017 | 5% | 50 |
| Glutamax 1-CTS | Gibco (Thermo Fisher Scientific, MA, USA) | A12860-01 | 1% | 10 |
| Pen-Strep | Thermo Fisher Scientific (MA, USA) | 15140-122 | 1% | 10 |
| N-acetyl cysteine | Sigma (Merck, USA) | A9165 | 0.8% | 8 |
| IL-2 | Thermo Fisher Scientific (MA, USA) | 200-02 | 200 IU | 0.152 |
| X-Vivo media | Lonza (Basel, Switzerland) | BE04-743Q | 92% | 1000 |

Typical activation and expansion experiments were performed in a 6-well format using a 2 mL seeding volume per well with a minimum of one additional replicate per condition tested. Dynabeads® Human T-Expander CD3/CD28 (Catalog #111.41D, ThermoFisher, USA) were prepared according to the manufacturer's instructions. Briefly, a bead aliquot was washed with 0.3 mL complete media three times, with supernatant wash removal occurring after sample application to DynaMag-2 permanent magnet (ThermoFisher Scientific, USA). After resuspension in complete media, a 60 μL bead slurry aliquot was added per well such that an approximate 3:1 bead-to-cell ratio was used for initial activation conditions (starting with $2 \times 10^6$ total cells per well).

Figure 3A:
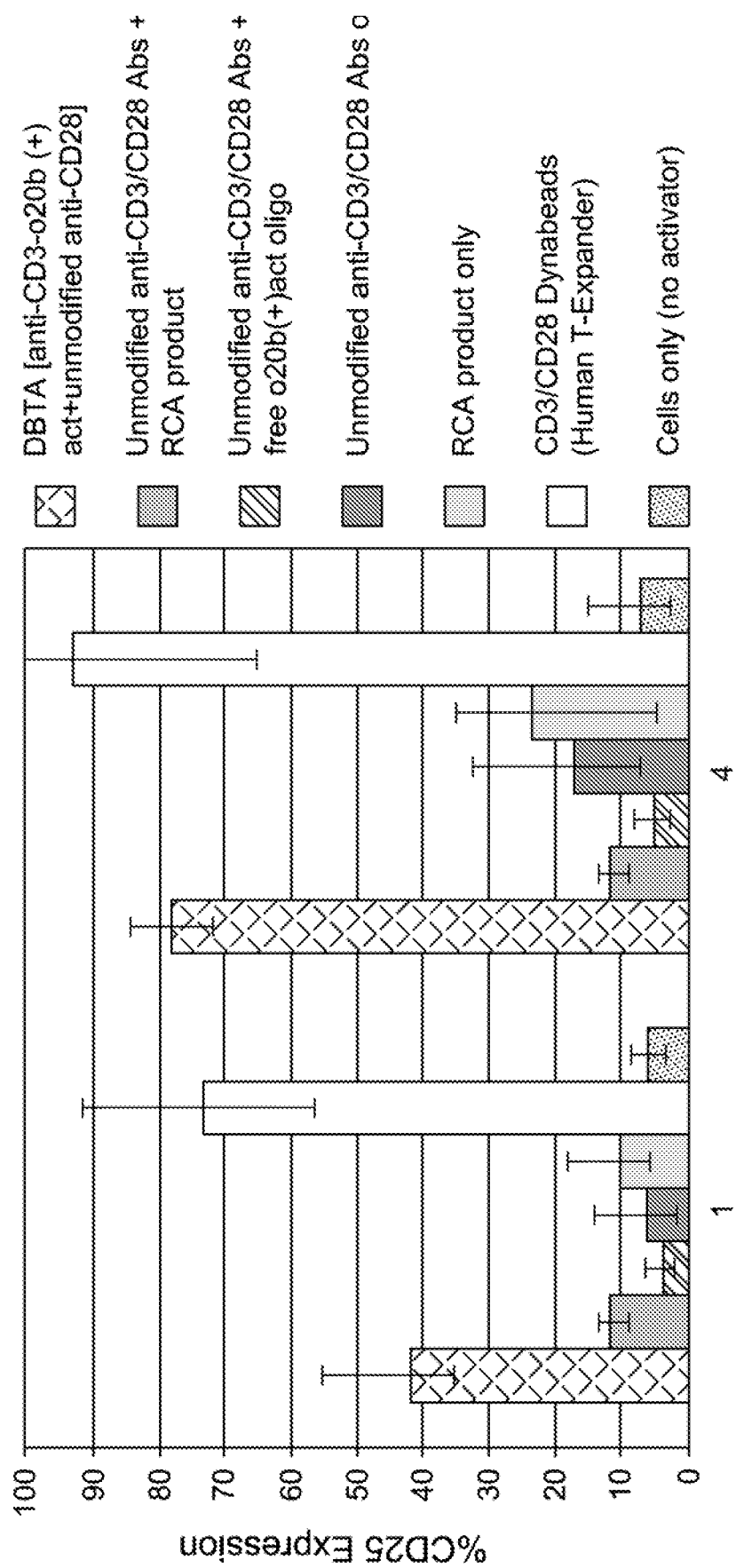
Figure 3B:
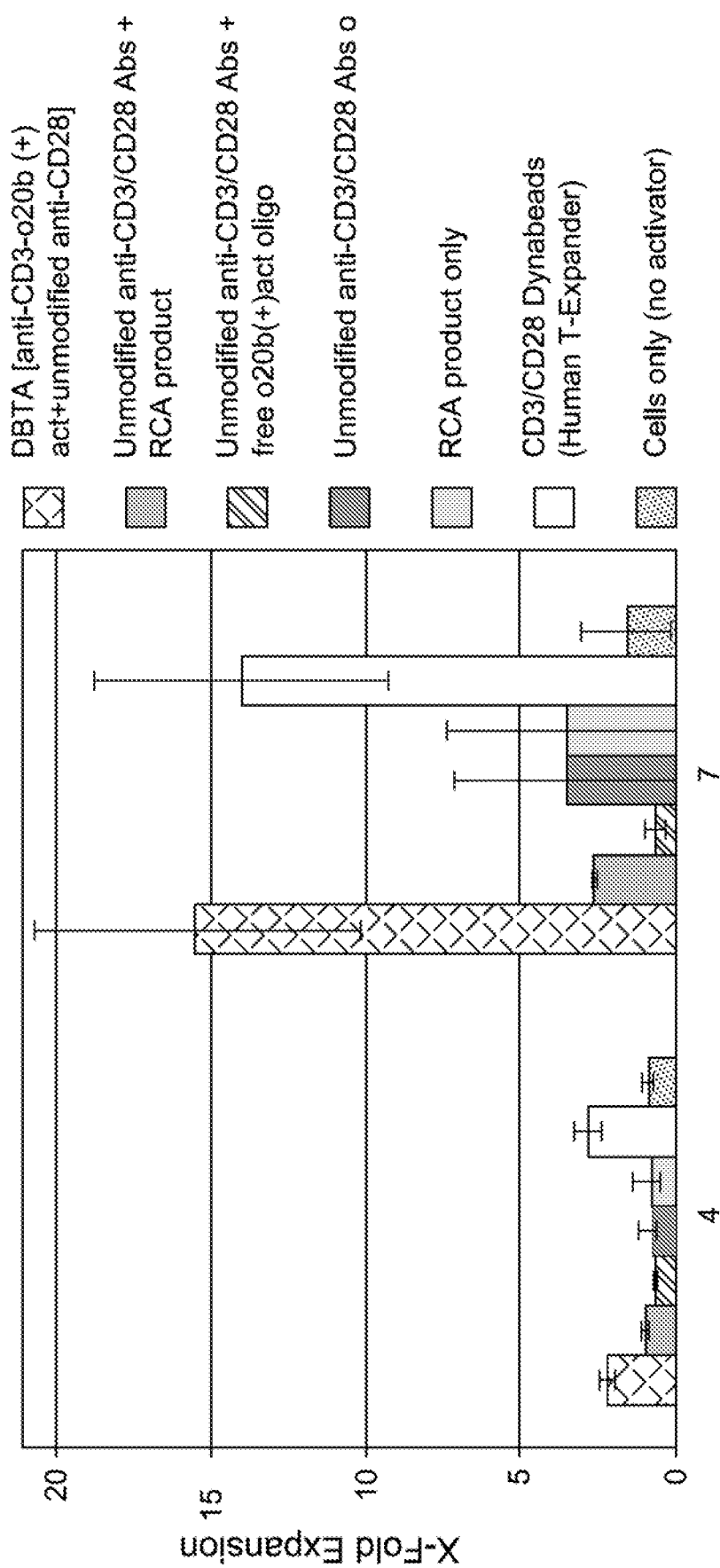
Figure 4A:
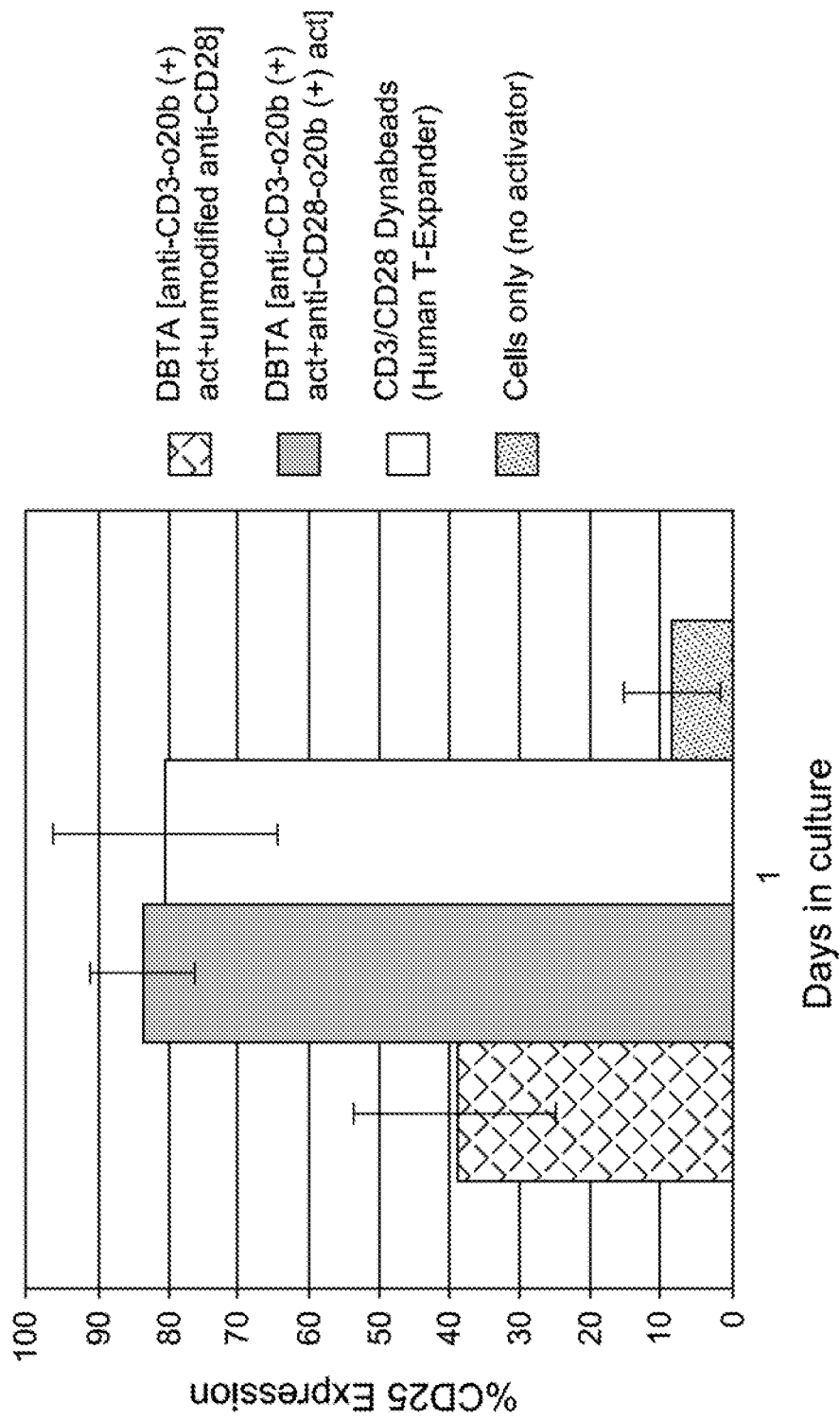
FIG. 4B is a graphical representation of the same cultures as in FIG. 4A after 4 and 7 days showing cell expansion represented as number of folds of expansion relative to a starting cell count.
Figure 4B:
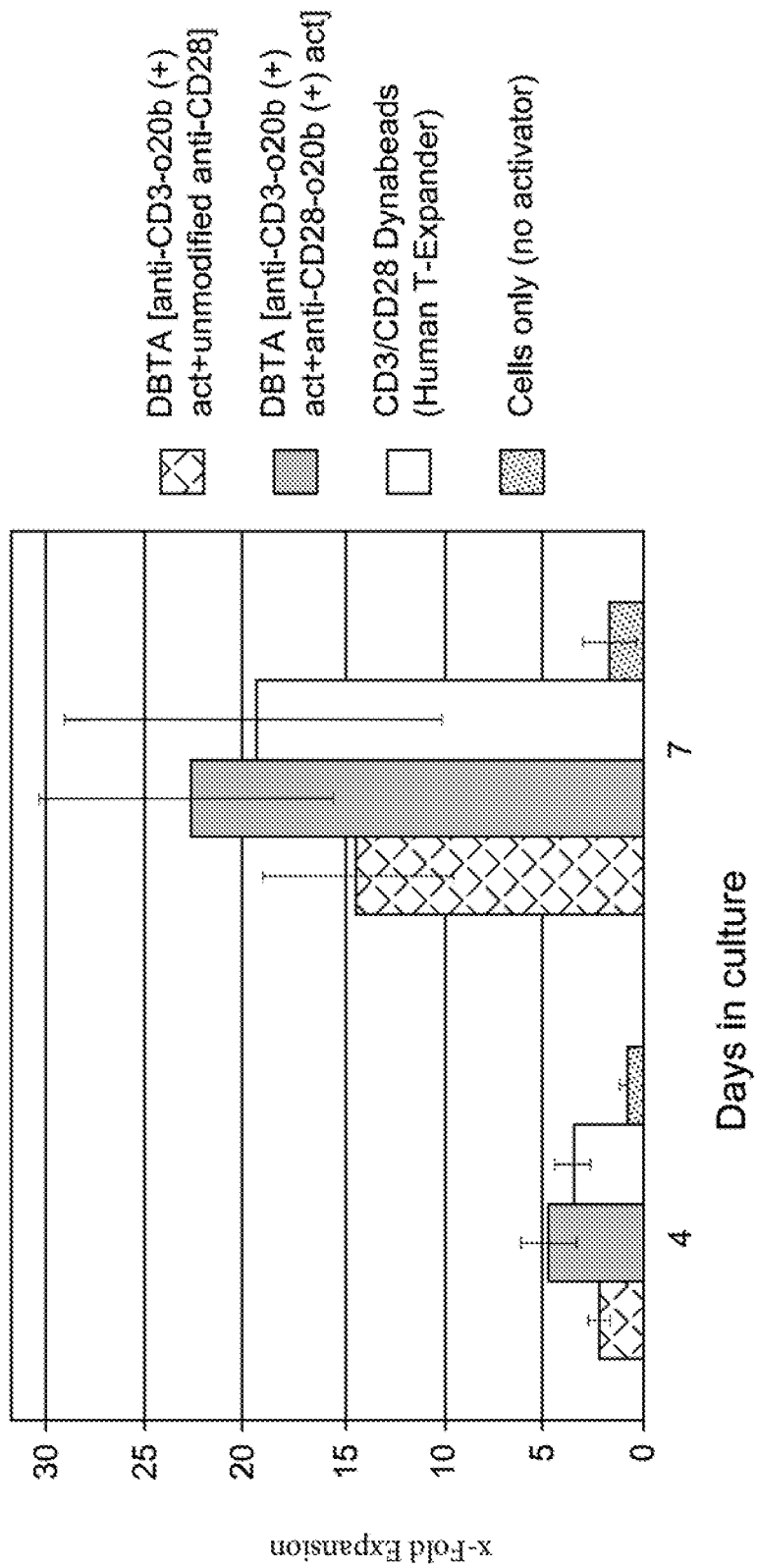

Unless otherwise specified, aliquots of DBTA components (anti-CD3-DNA, unmodified anti-CD28 or anti-CD28-DNA, and RCAact) were added separately and consecutively to cells directly from their respective stock solutions (stored at 4° C.). Additions of each DBTA component may be made in any sequential order. Standard initial concentrations of DBTA components were as follows: 1 μg/mL (6.7 nM) each for anti-CD3-o20b(+)act and anti-CD28-o20b(+)act with 10-fold molar excess of RCAact (~67 nM). RCAact concentration is based on the molar concentration of the repeating 43-base oligonucleotide and independent of total RCA product length or polydispersity. Following the addition of all the appropriate DBTA components, the well contents were mixed with a 1 mL pipette. The plates were then incubated at 37° C. and 5% $CO_2$ atmosphere under static conditions for 1-7 days or longer with periodic aliquots taken and, dilutions done with fresh media as needed for continuing expansion and analysis. Confirmation of cell activation was achieved by measuring CD25 expression using flow cytometry after 24 h incubation (day 1) and followed by additional measurements, if needed, at days 4 and 7. Cell counts, viability, and size (blasting) were additionally measured at days 4 and 7 using the Nucleocounter (ChemoMetec, Allerod, Denmark). Based on day 4 cell counts, a 1:4 or 1:8 dilutions with fresh complete media was performed to reduce cell density to 250,000 cells/mL per well. This enabled cells to expand in the exponential phase, without overgrowth, until day 7 analysis. For the negative control ("cells-only" sample group in which no activating agents were added), cell density was maintained at a minimum of 500,000 cells/mL. Further phenotypic analysis via flow cytometry was conducted at day 7 for select samples of interest. The panel of cell surface markers under investigation includeed CD4, CD8, CD27, CD28, CD3, CD57, CD25, and CD62L. FIG. 3A and FIG. 3B show significant activation and expansion was achieved with a DBTA system wherein only the anti-CD3 antibody was conjugated to the o20b(+)act and anti-CD28 was added as an unmodified soluble antibody (DBTA[anti-CD3-o20b(+)act+ unmodified anti-CD28]). Experiments were carried out with Dynabeads® Human T-Expander CD3/CD28 as control when comparing CD25 expression at days 1 and 4 and x-fold cell expansion at days 4 and 7. Control samples with unmodified antibodies, RCAact alone, unmodified antibodies with unconjugated binder nucleic acid sequence (free o20b(+)act) and cells showed very low level of activation and expansion, as expected. FIGS. 3A and 3B includes data from five separate experiments, seven individual human T cell donors, and 4 different batches of antibody conjugates. FIG. 4A and FIG. 4B show that the best performance was achieved with a DBTA composition where both anti-CD3 and anti-CD28 antibodies were attached to binder DNA sequence (DBTA [anti-CD3-o20b(+)act+anti-CD28-o20b(+)act]). The data for FIG. 4A and FIG. 4B represents averages taken from over 5 separate experiments encompassing over six individual human T cell donors.

Example 5: Comparison of Large-Scale T Cell Activation and Expansion Using Dynabeads® (ThermoFisher Scientific, Waltham, Mass., USA) Human T-Expander CD3/CD28 and a DBTA System of Nucleic Acid Polymers (RCAact) with Ab-DNA Conjugates (Anti-CD3-o20b(+)Act and Anti-CD28-o20b(+)Act)

In addition to 6-well plate studies as illustrated in Example 4, a large-scale comparison of T cell activation and expansion efficiency using 72C VueLife® bags (CellGenix GmbH, Breisgau, Germany) was performed. The same ratios and components described in Example 4 were scaled linearly to accommodate starting conditions of $32 \times 10^6$ cells in 32 mL of complete X-Vivo media ($1 \times 10^6$ cells/ml). The cultures were maintained in the 72C VueLife bags (CellGenix GmbH, Breisgau, Germany) within a standard cell culture incubator. On Day 4, cells were collected, washed with fresh media, counted, diluted in appropriate media volume to give $0.5 \times 10^6$ cells/mL and re-seeded within the VueLife 72C bag. On Day 6, cells were diluted and seeded in 250 mL in the Wave bag, on a rocking WAVE Bioreactor™ platform (GE Healthcare, Bio-Sciences) for further expansion. By Day 8, cells were counted using Nucleocounter® (ChemoMetec, Allerod, Denmark) and examined by flow cytometry for various CD surface marker expression. The tables 3-5 below depict comparable levels of CD25 expression, x-fold expansion, cell size, and viability for both Dynabeads® samples and those activated with DBTA. In addition, the day 8 flow analysis shows nearly identical levels of phenotypic expression for the full panel of CD markers for both Dynabeads® and DBTA. The preparation and results are illustrated in Tables 3-5 below.

TABLE 3

Cell Counts at 4 and 8 days.

| Sample | % CD25 (24 h) | Cell counts | | | Fold X | |
| --- | --- | --- | --- | --- | --- | --- |
| | | Day 4 (cells/mL) | Day 4 (total viable cells) | Day 8 (cells/mL) | Day 4 | Day 8/ Day 6 |
| DBTA [(anti-CD3-o20b(+)act + anti-CD28-o20b(+)act] | >90% | 8.45E+05 | 4.23E+07 | 1.57E+06 | 1.32 | 6.04 |
| Dynabeads ® | >90% | 1.25E+06 | 6.25E+07 | 1.38E+06 | 1.95 | 5.31 |

TABLE 4

Cell Viability as a percentage of population.

| Sample | Day 8 total Viable Cells | Cells size (μm) | | % Viability | |
| --- | --- | --- | --- | --- | --- |
| | | Day 4 | Day 8 | Day 4 | Day 8 |
| DBTA[(anti-CD3-o20b(+)act + anti-CD28-o20b(+)act] | 3.93E+08 | 12.2 | 10.9 | 98.1 | 97.5 |
| Dynabeads ® | 3.45E+08 | 12.1 | 11.0 | 97.6 | 97.1 |

TABLE 5

Cell Flow Cytometry results at 8 days.
Flow Cytometry Results at day 8
(% cells positive):

| CD Marker | DBTA | Dynabeads ® |
| --- | --- | --- |
| CD8 | 46% | 45% |
| CD4 | 51% | 53% |
| CD3 | 96% | 98% |
| CD25 | 80% | 84% |
| CD57 | 10% | 8% |
| CD62L | 95% | 96% |
| CCR7 | 62% | 47% |
| CD28 | 96% | 95% |
| CD27 | 98% | 96% |
| CD27$^+$ CD28$^+$ | 90% | 82% |

Example 6: The Effect of Adding Pre-Associated DBTA Components Together Prior to Cell Culture Addition Versus Separate Addition of all DBTA Components at the Start of Activation A series of T cell activation experiments were conducted to assess the effect of pre-incubating or pre-associating all of the DBTA system components (e.g., anti-CD3-DNA (anti-CD3-o20b(+)act), anti-CD28-DNA (anti-CD28-o20b(+)act), and RCAact) and then adding the pre-associated complex to T cells. The results were compared to the standard protocol of separate addition of each separate component to T cells for in situ association. For these pre-associated samples, the same quantities and ratios of DBTA components as used in Example 4 were added together in a 1.5 mL tube, mixed thoroughly, and incubated at room temperature for 30 min. The pre-associated DBTA mixture was then added to fresh T cell cultures in the 6 well-plates. In parallel, and as conducted in Example 4, standard DBTA samples not subjected to pre-association were added to T cell cultures. The results were compared to Dynabeads® and cells only control samples (positive and negative controls, respectively).

Figure 5A:
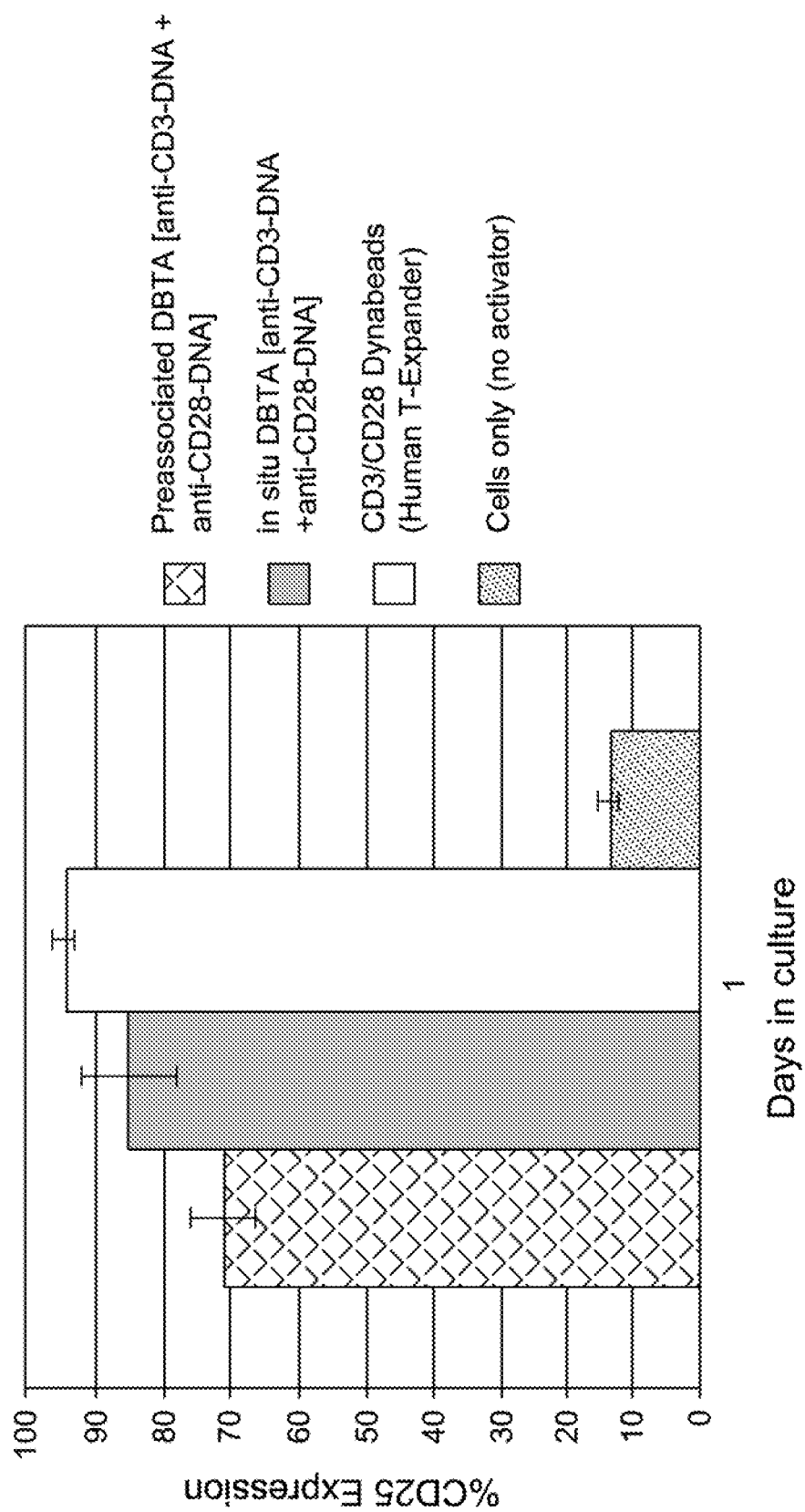
FIG. 5A is a graphical representation showing a trend towards higher activation after 1 day when the DBTA components were separately added to cells and associated in situ (denoted by "in situ DBTA[anti-CD3-o20b(+)act+anti-CD28-o20b(+)act]") compared to when they were pre-associated (denoted by "Preassociated DBTA[anti-CD3-o20b(+)act+anti-CD28-o20b(+)act]") before addition to cells.
Figure 5B:
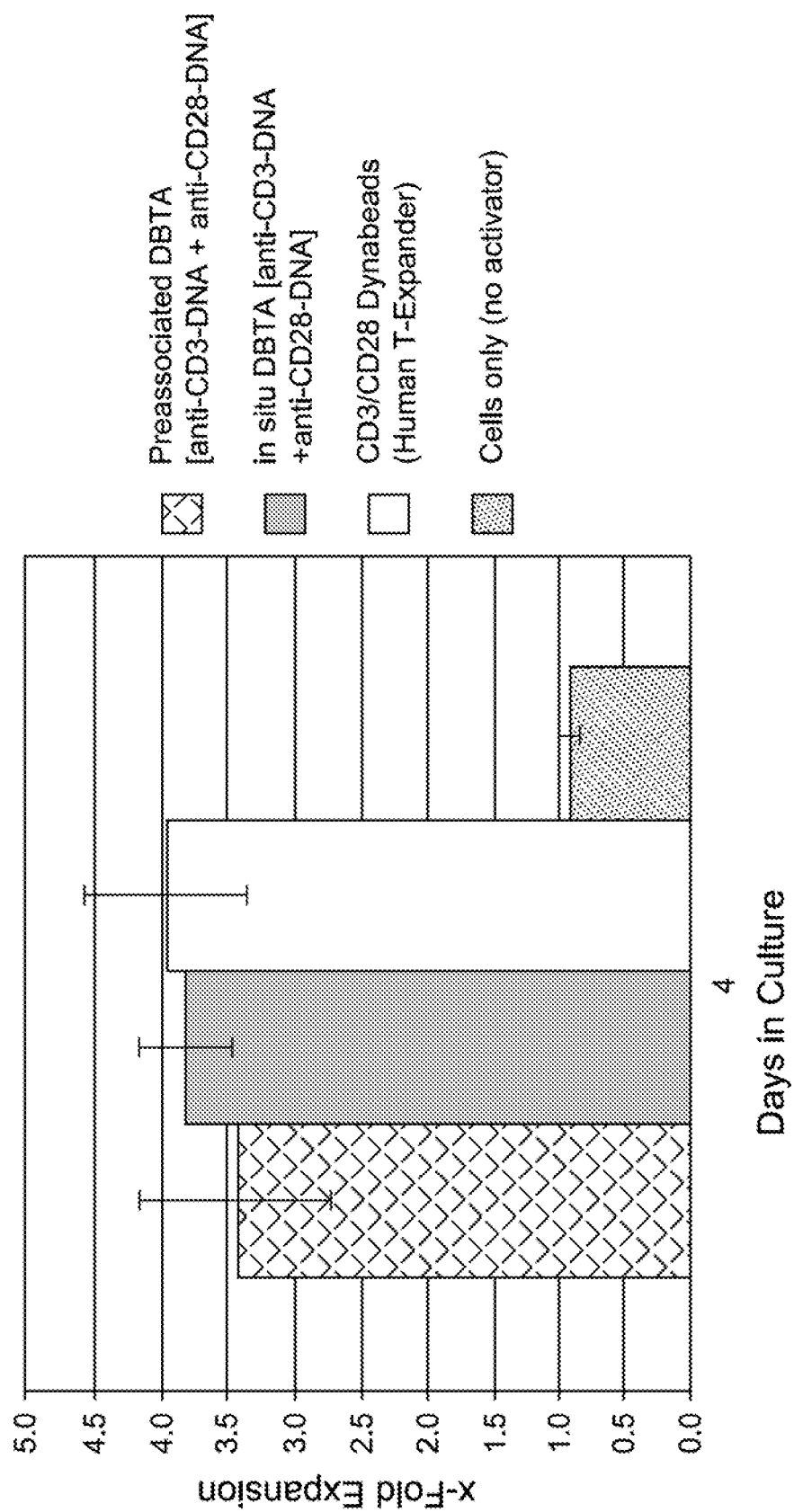
FIG. 5B is the same cultures as in FIG. 5A after 4 days showing cell expansion represented as number of folds of expansion relative to a starting cell count.

FIG. 5A and FIG. 5B shows that comparable levels of early activation (CD25 expression at 24 hour) and day 4 cell expansion is achieved whether or not the all the DBTA components (anti-CD3-DNA, anti-CD28-DNA and RCAact) are pre-incubated/pre-associated before addition (preassociated DBTA[anti-CD3-DNA+anti-CD28-DNA]) or added separately for in situ association (in situ DBTA [anti-CD3-DNA+anti-CD28-DNA]). FIG. 5A shows the CD25 expression after 24 hour incubation and FIG. 5B shows the cell expansion after 4 days. Both sets of DBTA samples caused significant activation and expansion of T cells. This data was derived from two separate experiments featuring four different human T cell donors and four different batches of Ab-DNA conjugates.

Example 7: Effect of Different Input DBTA Components (Ab-DNA Conjugate and RCAact) Quantities on T Cell Activation Efficiency A series of T cell activation experiments were conducted to assess the effect of different ratios of anti-CD3-DNA: anti-CD28-DNA on T cell activation and expansion. In all the cases the RCAact concentration was maintained at 67 nM, while 1:1 versus 1:2 molar ratios of anti-CD3-DNA: anti-CD28-DNA conjugate were examined. All other protocol conditions outlined in Example 4 were maintained.

FIG. 6A and FIG. 6B show that sufficient T cell activation (CD25 expression at 24 hour) and cell expansion (at days 4 and 7) respectively were achieved at a variety of input quantities of Ab-DNA and RCAact. As shown in the FIG. 6A and FIG. 6B: i) anti-CD3-DNA:anti-CD28-DNA (1:1) denotes a study where both the Ab-DNA conjugates were at a concentration 1 μg/mL (6.7 nM), ii) anti-CD3-DNA:anti-CD28-DNA (1:2) denotes anti-CD3-DNA at concentration 1 μg/mL and anti-CD28-DNA at concentration 2 μg/mL; iii) anti-CD3-DNA:anti-CD28-DNA (0.5:1) denotes anti-CD3-DNA at concentration 0.5 μg/mL and anti-CD28-DNA at concentration 1 μg/mL; iv) anti-CD3-DNA:anti-CD28-DNA (0.25:0.5) denotes anti-CD3-DNA at concentration 0.25 μg/mL and anti-CD28-DNA at concentration 0.5 μg/mL; and v) anti-CD3-DNA:anti-CD28-DNA (0.25:0.25) denotes anti-CD3-DNA at concentration 0.25 μg/mL and anti-CD28-DNA also at concentration 0.25 μg/mL. The lowest levels of CD25 expression (60%) was achieved with the lowest input quantities of Ab-DNA conjugates (0.25 μg/mL input or ~1.7 nM) and RCAact (~67 nM) (shown as anti-CD3-DNA: anti-CD28-DNA (0.25:0.25)). However, this level of activation still exceeded the cells-only negative control (20%). It is noted that significant activation (90% in terms of CD25 expression) was achieved even by using lower than the standard input quantity of anti-CD3-DNA conjugate (0.5 μg/mL) (shown as anti-CD3-DNA: anti-CD28-DNA (0.5:1)). The data for this example were derived from three separate experiments featuring five different human T cell donors and four different batches of Ab-DNA conjugates. CD3/CD28 Dynabeads® and cells only samples were used as positive and negative controls respectively.

Example 8: Effect of Pre-Incubating DBTA Antibody Conjugates with T Cells Prior to the Addition of RCA Polymeric Product for T Cell Activation An experiment was conducted to assess the effect of adding the anti-CD3-DNA and anti-CD28-DNA antibody conjugates to T cell culture to generate a Ab-DNA/cell pre-incubated sample prior to a separate, second addition of the rolling circle amplification product (RCAact) 30 min. later. The anti-CD3-DNA: anti-CD28-DNA ratio used for this study was 1:1. The results were compared to the procedure where all the DBTA components were added separately and simultaneously for in situ association. For this experiment, all other protocol details and quantities outlined in Example 4 were followed. For the in situ association protocol, anti-CD3-DNA: anti-CD28-DNA ratios used were 1:1 and 1:2.

FIG. 7A highlights a lower early activation (CD25 expression at 24 h) and FIG. 7B shows diminished expansion at day 7 cell for the Ab-DNA/cell pre-incubated sample (Cells-DBTA pre-incubated [anti-CD3-DNA: anti-CD28-DNA (1:1)) relative to the procedure where DBTA components were added simultaneously (denoted by in situ DBTA [anti-CD3-DNA: anti-CD28-DNA (1:1) and in situ DBTA [anti-CD3-DNA: anti-CD28-DNA (1:2)).

Example 9: Effect of Different Input Ab-DNA Conjugate-to-RCA Product Ratios on T Cell Activation Efficiency A series of T cell activation experiments were conducted to assess the effect of different Ab-DNA: RCAact input ratios on T cell activation efficiency. In all cases, only anti-CD3-DNA (anti-CD3-o20b(+)act) conjugates were used and has been denoted in the FIG. 8A and FIG. 8B as Ab-DNA. Each Ab-DNA conjugate sample, featured the same standard concentration per well for activation (1 µg/mL input or 6.7 nM) while a three-log range of input RCAact product was investigated (6.7 nM, 67 nM, and 670 nM). Rolling circle amplification products produced from RCA template containing CpG and RCA template containing no CpG (see, Example 1 and Table 1) were investigated. Using the rolling circle amplification product produced from RCA template containing no CpG, the following experimental conditions were used: i) Ab-DNA: RCAact at ratio 1:10 (denoted by No CpG, 1:10 Ab-DNA: RCA); ii) Ab-DNA: RCAact at ratio 1:1 (denoted by No CpG, 1:1 Ab-DNA: RCA); and iii) Ab-DNA: RCAact at ratio 1:100 (denoted by No CpG, 1:100 Ab-DNA: RCA). Similarly, for the rolling circle amplification product produced from CpG containing RCA template, the following experimental conditions were used: i) Ab-DNA: RCAact at ratio 1:10 (denoted by CpG, 1:10 Ab-DNA: RCA); ii) Ab-DNA: RCAact at ratio 1:1 (denoted by CpG, 1:1 Ab-DNA: RCA); and iii) Ab-DNA: RCAact at ratio 1:100 (denoted by CpG, 1:100 Ab-DNA: RCA). For both the sets of experiments, optimal T cell activation (measure by CD25 expression) was achieved at the Ab-DNA:RCAact ratio of 1:10. Diminished activation efficiency was observed at both higher and lower ratios of Ab-DNA RCA. All samples, however, demonstrated 10-fold or greater cell expansion at day 7 the experiment. All other protocol details and quantities outlined in Example 4 were maintained. FIG. 8A shows the % CD25 expression after 1 and 4 days of culture, and FIG. 8B shows the cell expansion after 4 and 7 days.

Example 10: Demonstration of Human T Cell Activation and Expansion Using an Alternative Rolling Circle Amplification Product Having Capture Oligonucleotides of Different Sequence and Length All previous examples (Examples 1-9) and associated figures (FIG. 1-8) for this disclosure utilize a DBTA system with rolling circle amplification product having sequences derived from human B-actin (Example 1). Successful human T cell activation and expansion may also be achieved with alternative capture nucleic acid polymers comprising capture oligonucleotides having various nucleotide sequence and lengths. One alternative example features rolling circle amplification products derived from the methicillin-resistant *Staphylococcus aureus* (MRSA) genome. The corresponding complementary first binder DNA sequence and second binder DNA sequence is referred to as o25b(+)mrsa (SEQ. ID. No. 7) and the corresponding DBTA products are referred to as DBTA[anti-CD3-o25b(+)mrsa+unmodified anti-CD28] or DBTA[anti-CD3-o25b(+)mrsa+anti-CD28-o25b(+)mrsa]. The specific sequence information for each of these DBTA components is shown in Table 6 below:

TABLE 6

Sequence Information.

| Name | sense | length (b) | Sequence (5'→3') including modifications | Use/ application |
|---|---|---|---|---|
| RCA primer (MRSA) (SEQ. ID. No 5) | − | 20 | ATC AAT GAT GCA TAA CAT CT | primer for RCA reactions, sequence derived from MRSA genome |
| RCA template (MRSA) (SEQ. ID. No 6) | + | 43 | /Phos/CAT CAT TGA TTT AGA CAC TGA AAA AGT TCG AGG AGA TGT TAT G | template for RCA reactions, sequence derived from MRSA genome |
| o25b(+) mrsa (SEQ. ID. No. 7) | + | 25 | /MalC6/CAT CAT TGA TTT AGA CAC TGA AAA A | conjugation to Ab via 5'-maleimide and binding to MRSA-derived RCA product |

FIG. 9A and FIG. 9B show significant performance of DBTA[anti-CD3-o25b(+)mrsa+unmodified anti-CD28] with respect to CD25 expression (FIG. 9A) after days 1 and 4, and x-fold cell expansion after days 4 and 7 (FIG. 9B). These results are comparable to the (3-actin derived DBTA system (DBTA[anti-CD3-o20b(+)act+unmodified anti-CD28]) shown in the above examples. Also, control experiments were performed with unmodified antibodies, rolling circle amplification product alone (RCA product only (MRSA)), and cells only negative controls. The negative controls showed very low levels of activation and expansion. It is noted that the exact same protocol was followed for the synthesis of Ab-DNA, for the rolling circle amplification process, and for the cell culturing protocols including molar quantities as described above for (3-actin DBTA.

Example 11: Demonstration of Human T Cell Activation and Expansion Using MRSA-Based DBTA Composition, DBTA[Anti-CD3-o25b(+)Mrsa+Unmodified Anti-CD28] Featuring Cleaved Rolling Circle Amplification Products A comparison of human T cell activation and expansion efficiency using different sized rolling circle amplification (RCA) products was conducted using the MRSA-based DBTA system (See, Example 10 and Example 3 for general conditions used to generate a full length RCA product). For these experiments, full length RCA products were subjected to sonication conditions yielding different relative size distributions. To produce sonicated RCA products, a Covaris M220 Focused Ultrasonicator™ (Covaris, Woburn, Mass.) was utilized according to the manufacturer's recommended input conditions to yield 1500 bases (b) and 150 bases (b) sized fragments starting from large genomic DNA fragments. Target input parameters include peak incident power, duty factor, cycles per burst, treatment time, and temperature. After sonication, analytical size exclusion chromatography was used according to Example 1 conditions to confirm the relative size distributions of products. While absolute size and molecular weight determinations are unknown for the RCA products by this method, the expected general trend of increasing elution time for smaller fragments was observed. The following elution times were thus observed: 10.1 min. (corresponding to the void volume) for ~16 Kb (theoretical maximum length) full length RCA product, 10.8 min. for the 1.5 Kb sonicated RCA product, 14.8 min. for the 0.15 Kb sonicated RCA product, 19.2 min. for the starting 43-base RCA template (control injection), 20.0 min. for the unconjugated o25b(+)mrsa (control injection), and 23.7 min. for residual small molecules including nucleotides. The 1.5 Kb sonicated product was also sized by gel electrophoresis and was found to contain fragments ranging in size from 400-1600 bases (close to the targeted range of 1.5 Kb) as expected as sonication doesn't provide a single length product.

FIG. 10A and FIG. 10B show that larger the RCA product, higher the activation (see, FIG. 10A % CD25 expression) and expansion after days 1 and 4. However, the trend becomes less pronounced later in the study. In particular, by day 7, all the three RCA products of different sizes yield comparable levels of cell expansion (FIG. 10B).

Example 12: Controlling T Cell Activation by Changing the Amount of Binder DNA Sequence Attached to Each T Cell Activator and/or T Cell Co-Stimulator Experimental conditions for the synthesis of anti-CD3 antibody attached first binder DNA sequence (anti-CD3-o20b(+)act) and anti-CD28 antibody attached second binder DNA sequence (anti-CD28-o20b(+)act) were as described in Example 1 except that the antibody-DNA conjugates were prepared to yield varying DNA (D): antibody (P) ratio. This was done with the intent of controlling the level of hybridization of the anti-CD3 antibody attached first binder DNA and the anti-CD28 antibody attached second binder DNA sequence with the rolling circle amplification product. FIG. 11 shows the performance of DBTA[anti-CD3-o20b(+)act+anti-CD28-o20b(+)act] at two different D/P ratios. T cell activation, as measured by CD25 expression was higher at D/P ratios of 2.8-3.0 (denoted by DBTA[anti-CD3-o20b(+)act+anti-CD28-o20b(+)act] (D/P 2.8-3.0)) compared to D/P ratios of 1.5-1.8 (denoted by DBTA[anti-CD3-o20b(+)act+anti-CD28-o20b(+)act] (D/P 1.5-1.8)). The T cell activation observed was higher at higher D/P ratio. The data for FIG. 11 represents averages taken from 8 separate experiments.

Example 13. T Cell Activation and Expansion Using Ab-DNA Conjugates and Cationic Capture Polymers Experimental conditions for the synthesis of anti-CD3-o20b(+)act and anti-CD28-o20b(+)act have been described in Example 1. Commercially available Jet PEI® (VWR International, Pennsylvania, USA, Catalog Number 89129-914) and Poly-L-lysine (PLL) (Sigma-Aldrich, Missouri, USA, Catalog Number P9155) were used as the second agent for this experiment. The N/P ratios (the ratios of moles of the amine groups of cationic capture polymers to those of the phosphate ones of binder DNA sequence) used in this study were: N/P of 3 for jet PEI® and N/P of 1 for PLL. The anti-CD3-o20b(+)act and anti-CD28-o20b(+)act conjugates were used at a concentration of 1 μg/mL. All protocol details and quantities outlined in Example 1 were followed. For T cell activation, the protocol described in Example 4 was followed. FIG. 12A and FIG. 12B show the activation and proliferation of T cells using anti-CD3-o20b(+)act, anti-CD28-o20b(+)act and cationic capture polymers (PEI or PLL).

Example 14: Controlling CD4:CD8 T Cell Ratio

Frozen aliquots of human Pan T Cells from AllCells (Catalog #PB009-IF) were used for all activation and expansion studies. Pan T Cells are thawed and processed as described in Example 2 and added to following complete X-Vivo media to give an initial concentration of $1 \times 10^6$ cells/mL.

Typical activation and expansion experiments are performed in a 6-well format using a 2 mL seeding volume per well with a minimum of one additional replicate per condition tested. Unless otherwise specified, aliquots of DBTA components (anti-CD3-DNA, anti-CD28-DNA, and RCAact) were added separately and consecutively to cells directly from their respective stock solutions. Additions of each DBTA component may be made in any sequential order. Standard initial concentrations of DBTA components were as follows: 1 μg/mL (6.7 nM) for anti-CD3-DNA and anti-CD28-DNA, with 10-fold molar excess of RCAact (~67 nM). RCAact concentration was based on the molar concentration of the repeating 43-base segment and independent of total RCA product length or polydispersity. Anti-4-1BB antibody was used as the T cell co-stimulator in some experiments. Anti-4-1BB-DNA was synthesized by a protocol described in Example 1. Anti-4-1BB-DNA was used at a concentration of 100 ng/mL. Following the addition of all of the appropriate activating components, the well contents were mixed with a 1 mL pipette. The plates were then incubated at 37° C. and 5% $CO_2$ atmosphere under static conditions for 1-7 days or longer with periodic aliquots taken and, dilutions done with fresh media as needed for continuing expansion and analysis.

T cell activation was measured by CD25 expression using flow cytometry after 24 h incubation, followed by additional measurements, if needed, at days 4 and 7. The ratio of CD4:CD8 T cells was followed by flow cytometry using fluorescent dye conjugated anti-CD4 and anti-CD8 antibodies. Cell counts, viability, and size (blasting) were additionally measured at days 4 and 7 using the Nucleocounter. Based on day 4 cell counts, a 1:4 or 1:8 dilution with fresh complete media was performed to reduce cell density to 250,000 cells/mL per well. This enabled cells to expand in the exponential phase, without overgrowth, until day 7 analysis. For the negative control ("cells only") sample group in which no activating agents were added, cell density was maintained at a minimum of 500,000 cells/mL.

FIG. 13A and FIG. 13B shows the expansion of CD4 and CD8 T cells over a 7-day expansion period using DBTA [anti-CD3-o20b(+)act+anti-CD28-o20b(+)act], and DBTA [anti-CD3-o20b(+)act] respectively. A higher proportion of CD8 cells (relative to day 1) was observed at day 7 when the DBTA[anti-CD3-o20b(+)act] is used in an IL-2 based medium. FIG. 14 shows another way to further increase the proportion of CD8 cells over CD4 cells by using DBTA [anti-CD3-o20b(+)act+anti-4-1BB-o20b(+)act].

Example 15: T Cell Activation Using a System Comprising a First Binder DNA Sequence and/or a Second Binder DNA Sequence Attached to a Secondary Antibody (Secondary Ab-DNA Conjugate) and Unmodified Anti-CD3 and Anti-CD28 Antibodies Attachment of first binder DNA and/or second binder DNA sequence to a secondary antibody to generate a secondary Ab-DNA conjugate:

Secondary antibodies targeting different mouse IgG subtypes (Goat anti mouse IgG (H+L), catalog #115-005-062, Goat anti-mouse IgG1, catalog #115-005-205, Goat anti-mouse IgG (1+2a+2b+3), catalog #115-005-164 and Goat anti-mouse IgG2a, catalog #115-005-206), were obtained from Jackson Immunoresearch and conjugated to the binder DNA sequence, o20b(+)act, as described above in Example 1 for the anti-CD3 and anti-CD28 conjugates.

T cell activation was performed as described in Example 4 using the following components, i) secondary Ab-DNA conjugate (anti-IgG2α-o20b(+)act) at 2 or 4 µg/mL, ii) unmodified primary antibodies anti-CD3 and anti-CD28 at 1 µg/mL concentration and iii) 10-fold molar excess (with respect to primary antibodies anti-CD3 and anti-CD28) of RCAact. Cells only and CD3/CD28 Dynabeads® were used as negative and positive controls respectively. DBTA[anti-CD3-o20b(+)act+anti-CD28-o20b(+)act] and a mixture of unmodified anti-CD3 (1 µg/mL), anti-CD28 (1 µg/ml) and IgG2-specific secondary (4 µg/mL) antibodies were used as two additional controls. FIG. 15 shows that similar levels of activation can be achieved using a secondary Ab-DNA conjugate, unmodified anti-CD3 and anti-CD28 antibodies, and RCAact as is achieved using the DBTA composition of example 4.

Example 16: Activation of Natural Killer Cells

Secondary antibodies targeting mouse IgG1 subtypes (Goat anti-mouse IgG1, catalog #115-005-205), was obtained from Jackson Immunoresearch and attached to the binder DNA sequence o20b(+)act as described above in Example 1 for the attachment of anti-CD3 and anti-CD28 antibodies to the binder DNA sequence.

Frozen aliquots of Peripheral Blood CD56+CD16+natural killer cells (Lonza, Basel, Switzerland, Catalog #2W-501) were used for the activation study. Medium used was X-Vivo 20 (Lonza, Basel, Switzerland, Catalog #04-448Q) supplemented with 5% Human serum off the clot (Valley Biomedical, VA, USA, Catalog #HS1017) and 500 IU/mL of IL-2 (Peprotech, N.J., USA, Catalog #200-02). Activation experiments were performed in 48 well-plates using a 500 µL seeding volume and a density of $10^6$ cells/mL. For activation, two combinations of primary antibodies were used: i) anti-CD335+anti-CD2 and ii) anti-CD335+anti-CD244. The anti-CD335 was obtained from eBioscience™ (Thermo Fisher Scientific, Waltham, Mass., USA, Catalogue #16-3359-85). Anti-CD2 was obtained from Becton Dickinson (NJ, USA, Catalog No. 555323) and anti-CD244 from eBioscience™ (Thermo Fisher Scientific, Waltham, Mass., USA, Catalog #: 16-5838-85). Natural killer cell activation was performed using the following components, secondary Ab-DNA conjugate (IgG1-o20b(+)act), unmodified primary antibodies combinations (anti-CD335+anti-CD2; or anti-CD335+ and anti-CD244) and RCAact. Control groups had the soluble antibodies alone or the cells only samples. Concentrations of antibodies used for the study are shown in Table 7.

TABLE 7

Concentrations of the components used for the natural killer cell activation study

| Groups | RCAact | Anti-CD335 | Second primary Ab | Concentration of second primary Ab | Anti-IgG1-o20b(+)act |
|---|---|---|---|---|---|
| Anti-IgG1-o20b(+)act + RCAact + anti-CD335+ and anti-CD2 | 67 nM | 1.0 µg/mL | anti-CD2 | 2.0 µg/mL | 8.0 µg/mL |
| Anti-CD335+ and anti-CD2 | — | 2.5 µg/mL | anti-CD2 | 5.0 µg/mL | — |
| Anti-IgG1-o20b(+)act + RCAact + anti-CD335+ and anti-CD244 | 67 nM | 2.5 µg/mL | anti-CD244 | 5.0 µg/mL | 20 µg/mL |
| anti-CD335+ and anti-CD244 | — | 2.5 µg/mL | anti-CD244 | 5.0 µg/mL | — |

Following the addition of all of the appropriate activating components, the well contents were mixed with a 1 mL pipette. The plates were then incubated at 37° C. and 5% CO2 atmosphere under static conditions for 24 hrs. Confirmation of cell activation was achieved by CD25 expression using flow cytometry after 24 h incubation (day 1). FIG. 15 shows higher CD25 expression with secondary antibody-DNA conjugates as compared to soluble antibodies and cells alone.

The invention claimed is:

1. A method of activating immune cells, the method comprising:
   a) providing a population of immune cells; and
   b) contacting the population of immune cells with a first agent and a second agent,
   wherein the first agent comprises an immune cell activator attached to a first binder moiety,
   wherein the second agent comprises at least one capture oligomer,
   wherein the at least one capture oligomer is capable of associating with the first binder moiety, and
   wherein the first binder moiety is a first binder nucleic acid sequence.

2. The method of claim 1, wherein the immune cell activator is attached to the first binder nucleic acid sequence via a covalent linkage.

3. The method of claim 1, wherein the immune cell activator is non-covalently attached to the first binder nucleic acid sequence via an intermediate binder moiety.

4. The method of claim 3, wherein the intermediate binder moiety is selected from a group consisting of a secondary antibody, a biotin, an avidin, and a combination thereof.

5. The method of claim 3, wherein the intermediate binder moiety is attached to the first binder nucleic acid sequence via a covalent linkage.

6. The method of claim 5, wherein the intermediate binder moiety is capable of attaching with the immune cell activator via a non-covalent interaction.

7. The method of claim 1, wherein the first agent is formed in situ in a medium containing the population of immune cells.

8. The method of claim 1, wherein the second agent is a capture nucleic acid polymer comprising at least one capture oligonucleotide and wherein the at least one capture oligonucleotide is complementary to the first binder nucleic acid sequence.

9. The method of claim 1, wherein the immune cell is a natural killer cell and the immune cell activator is a natural killer cell activator, wherein the natural killer cell activator is an anti-CD335 antibody, an anti-CD244 antibody, anti-CD2 antibody or combinations thereof.

10. A method of activating T cells, the method comprising:
    a) adding to a population of T cells, an anti-CD3 antibody, a first binder moiety attached to a secondary antibody, and a second agent comprising at least one capture oligomer; and
    b) incubating the population of T cells,
    wherein the secondary antibody is capable of attaching with the anti-CD3 antibody,
    wherein the at least one capture oligomer is capable of associating with the first binder moiety, and
    wherein the first binder moiety is a first binder nucleic acid sequence.

11. The method of claim 10, wherein the anti-CD3 antibody is attached to the first binder nucleic acid sequence via a covalent linkage.

12. The method of claim 10, wherein the anti-CD3 antibody is non-covalently attached to the first binder nucleic acid sequence via an intermediate binder moiety.

13. The method of claim 10, wherein the secondary antibody is non-covalently attached to the at least one capture oligomer via an intermediate binder moiety.

14. The method of claim 10, wherein the at least one capture oligomer is complementary to the first binder nucleic acid sequence.

* * * * *